(12) United States Patent
Cheng et al.

(10) Patent No.: US 10,631,717 B2
(45) Date of Patent: Apr. 28, 2020

(54) ENDOSCOPE SHEATH ARM

(71) Applicant: Gyrus ACMI, Inc., Southborough, MA (US)

(72) Inventors: Ming J. Cheng, W. Warwick, RI (US); Gregory S. Konstorum, Stamford, CT (US)

(73) Assignee: Gyrus Acmi, Inc., Southborough, MA (US)

( * ) Notice: Subject to any disclaimer, the term of this patent is extended or adjusted under 35 U.S.C. 154(b) by 0 days.

(21) Appl. No.: 16/106,390

(22) Filed: Aug. 21, 2018

(65) Prior Publication Data

US 2018/0353057 A1    Dec. 13, 2018

Related U.S. Application Data

(63) Continuation of application No. 14/493,700, filed on Sep. 23, 2014, now Pat. No. 10,098,524.

(60) Provisional application No. 61/882,652, filed on Sep. 26, 2013.

(51) Int. Cl.
| | |
|---|---|
| *A61B 1/015* | (2006.01) |
| *A61B 1/00* | (2006.01) |
| *A61B 1/06* | (2006.01) |
| *A61B 1/12* | (2006.01) |
| *A61B 90/70* | (2016.01) |

(52) U.S. Cl.
CPC .......... *A61B 1/015* (2013.01); *A61B 1/00068* (2013.01); *A61B 1/00119* (2013.01); *A61B 1/00135* (2013.01); *A61B 1/00142* (2013.01); *A61B 1/06* (2013.01); *A61B 1/126* (2013.01); *A61B 90/70* (2016.02); *A61B 1/00128* (2013.01); *A61B 2090/701* (2016.02)

(58) Field of Classification Search
CPC ............ A61B 1/00119; A61B 1/00128; A61B 1/00142; A61B 1/00147; A61B 1/00149
USPC ......................... 600/102, 121–125, 132, 136
See application file for complete search history.

(56) References Cited

U.S. PATENT DOCUMENTS

| 1,555,003 A | 9/1925 | Greenberg et al. |
| 2,112,056 A | 3/1938 | Frederick |
| 3,572,325 A | 3/1971 | Seymour et al. |
| (Continued) | | |

FOREIGN PATENT DOCUMENTS

| CN | 1719997 | 1/2006 |
| EP | 0374727 A1 | 6/1990 |
| (Continued) | | |

OTHER PUBLICATIONS

US 5,772,579 A, 06/1998, Reisdorf (withdrawn)
(Continued)

*Primary Examiner* — Timothy J Neal
*Assistant Examiner* — Jae Woo
(74) *Attorney, Agent, or Firm* — Schwegman Lundberg & Woessner, P.A.

(57) ABSTRACT

An endoscope sheath comprising: (a) a tube configured to receive all or a portion of a shaft of an endoscope, the endoscope including a light post in a proximal end region of the endoscope; and (b) an arm attached to and extending from a proximal end region of the sheath; wherein the arm has one or more features that are in communication with the light post to orient the sheath axially and rotationally with respect to the endoscope.

20 Claims, 8 Drawing Sheets

(56) References Cited

U.S. PATENT DOCUMENTS

| | | | | |
|---|---|---|---|---|
| 3,592,199 | A * | 7/1971 | Ostensen | A61B 1/267 362/197 |
| 3,610,478 | A * | 10/1971 | Johnston | B67D 1/0832 137/212 |
| 3,659,423 | A * | 5/1972 | Lair | F02K 9/84 239/265.19 |
| 3,675,641 | A * | 7/1972 | Fiore | A61B 1/31 600/184 |
| 3,689,083 | A * | 9/1972 | Greenawalt | F16J 15/38 277/372 |
| 4,254,762 | A | 3/1981 | Yoon | |
| 4,281,646 | A | 8/1981 | Kinoshita | |
| 4,312,375 | A | 1/1982 | Leinemann | |
| 4,548,197 | A | 10/1985 | Kinoshita | |
| 4,646,722 | A | 3/1987 | Silverstein et al. | |
| 4,850,342 | A | 7/1989 | Hashiguchi et al. | |
| 4,907,395 | A * | 3/1990 | Opie | A61B 1/00142 206/364 |
| 4,991,565 | A | 2/1991 | Takahashi et al. | |
| 5,167,220 | A | 12/1992 | Brown | |
| 5,170,774 | A | 12/1992 | Heckele | |
| 5,176,645 | A | 1/1993 | Guerrero | |
| 5,178,606 | A | 1/1993 | Ognier et al. | |
| 5,199,417 | A | 4/1993 | Muller et al. | |
| 5,207,213 | A | 5/1993 | Auhll et al. | |
| 5,225,001 | A * | 7/1993 | Manni | A61B 1/121 134/104.1 |
| 5,237,984 | A * | 8/1993 | Williams | A61B 1/00142 359/510 |
| 5,269,756 | A | 12/1993 | Dryden | |
| 5,313,934 | A | 5/1994 | Wiita et al. | |
| 5,328,458 | A | 7/1994 | Sekino et al. | |
| 5,354,267 | A | 10/1994 | Niermann et al. | |
| 5,377,668 | A * | 1/1995 | Ehmsen | A61B 1/00165 600/121 |
| 5,413,092 | A | 5/1995 | Williams, III et al. | |
| 5,419,309 | A * | 5/1995 | Biehl | A61B 1/00091 600/112 |
| 5,439,022 | A | 8/1995 | Summers et al. | |
| 5,486,155 | A * | 1/1996 | Muller | A61B 1/00135 600/105 |
| 5,505,707 | A | 4/1996 | Manzie et al. | |
| 5,509,892 | A | 4/1996 | Bonnet | |
| 5,518,501 | A * | 5/1996 | Oneda | A61B 1/00091 600/121 |
| 5,551,448 | A * | 9/1996 | Matula | A61B 17/0218 128/897 |
| 5,554,100 | A | 9/1996 | Peck et al. | |
| 5,554,112 | A | 9/1996 | Walbrink et al. | |
| 5,556,258 | A | 9/1996 | Lange et al. | |
| 5,575,756 | A * | 11/1996 | Karasawa | A61B 1/00068 600/121 |
| 5,593,404 | A | 1/1997 | Costello et al. | |
| 5,630,795 | A | 5/1997 | Kuramoto et al. | |
| 5,647,840 | A | 7/1997 | D'amelio et al. | |
| 5,662,588 | A * | 9/1997 | Iida | A61B 1/00091 600/121 |
| 5,681,262 | A | 10/1997 | Isse | |
| 5,690,605 | A * | 11/1997 | Hamlin | A61B 1/00142 600/109 |
| 5,695,448 | A * | 12/1997 | Kimura | A61B 1/0005 600/114 |
| 5,697,888 | A | 12/1997 | Kobayashi et al. | |
| 5,700,236 | A | 12/1997 | Sauer et al. | |
| 5,702,348 | A * | 12/1997 | Harhen | A61B 1/00131 600/121 |
| 5,779,625 | A | 7/1998 | Suzuki et al. | |
| 5,785,689 | A | 7/1998 | De Toledo et al. | |
| 5,792,045 | A * | 8/1998 | Adair | A61B 1/042 600/122 |
| 5,797,836 | A | 8/1998 | Lucey et al. | |
| 5,823,940 | A | 10/1998 | Newman | |
| 5,989,183 | A * | 11/1999 | Reisdorf | A61B 1/00091 600/121 |
| 6,110,103 | A * | 8/2000 | Donofrio | A61B 1/126 600/114 |
| 6,126,592 | A | 10/2000 | Proch et al. | |
| 6,181,442 | B1 | 1/2001 | Ogura et al. | |
| 6,196,967 | B1 | 3/2001 | Lim et al. | |
| 6,282,442 | B1 | 8/2001 | DeStefano et al. | |
| 6,354,813 | B1 | 3/2002 | Laing | |
| 6,447,446 | B1 * | 9/2002 | Smith | A61B 1/00142 600/118 |
| 6,478,731 | B2 * | 11/2002 | Speier | A61B 1/00135 600/121 |
| 6,558,379 | B1 | 5/2003 | Batchelor et al. | |
| 6,645,140 | B2 | 11/2003 | Brommersma | |
| 6,652,484 | B1 | 11/2003 | Hunckler et al. | |
| 6,824,544 | B2 | 11/2004 | Boebel et al. | |
| 6,911,005 | B2 * | 6/2005 | Ouchi | A61B 1/00142 600/121 |
| 7,160,247 | B2 | 1/2007 | Deppmeier et al. | |
| 7,192,396 | B2 * | 3/2007 | Boulais | A61B 1/00147 600/102 |
| 7,252,110 | B2 | 8/2007 | Semeia | |
| 7,270,647 | B2 | 9/2007 | Karpowicz et al. | |
| 7,413,542 | B2 | 8/2008 | Kucklick et al. | |
| 7,708,689 | B2 | 5/2010 | Deppmeier et al. | |
| 7,736,301 | B1 * | 6/2010 | Webler | A61B 5/0062 385/53 |
| 7,758,497 | B2 * | 7/2010 | Hem | A61B 1/00094 600/104 |
| 7,766,819 | B2 | 8/2010 | Matsumoto | |
| 7,811,228 | B2 | 10/2010 | Adams | |
| 7,942,814 | B2 * | 5/2011 | Remijan | A61B 1/00135 600/121 |
| 8,001,984 | B2 * | 8/2011 | Sasaki | A61B 1/00091 134/102.1 |
| 8,029,438 | B2 | 10/2011 | Hagihara et al. | |
| 8,047,215 | B1 | 11/2011 | Sasaki | |
| 8,079,952 | B2 | 12/2011 | Fujimoto | |
| 8,231,574 | B2 | 7/2012 | Haack et al. | |
| 8,231,658 | B2 * | 7/2012 | Oskin | A61B 1/00135 600/125 |
| 8,337,470 | B2 | 12/2012 | Prasad et al. | |
| 8,393,328 | B2 | 3/2013 | Angel et al. | |
| 8,394,013 | B2 | 3/2013 | Ichimura | |
| 8,409,109 | B2 | 4/2013 | Tiesma et al. | |
| 8,419,624 | B2 | 4/2013 | James et al. | |
| 8,663,090 | B2 * | 3/2014 | Fujimoto | G02B 23/2476 600/114 |
| 8,870,752 | B2 * | 10/2014 | Avitsian | A61B 1/00078 600/121 |
| 8,888,689 | B2 * | 11/2014 | Poll | A61B 1/00091 600/159 |
| 8,911,415 | B2 | 12/2014 | Knapp | |
| 9,078,562 | B2 * | 7/2015 | Poll | A61B 1/00119 |
| 9,155,453 | B2 | 10/2015 | Kumar et al. | |
| 9,332,894 | B2 | 5/2016 | Cheng et al. | |
| 10,022,040 | B2 | 7/2018 | Cheng et al. | |
| 10,028,644 | B2 | 7/2018 | Konstorum et al. | |
| 10,098,524 | B2 | 10/2018 | Cheng et al. | |
| 10,478,052 | B2 | 11/2019 | Konstorum et al. | |
| 2001/0000041 | A1 | 3/2001 | Selmon et al. | |
| 2001/0011162 | A1 | 8/2001 | Epstein | |
| 2002/0120180 | A1 * | 8/2002 | Speier | A61B 1/00135 600/125 |
| 2002/0166946 | A1 * | 11/2002 | Iizuka | A61B 1/00087 250/201.2 |
| 2004/0073088 | A1 * | 4/2004 | Friedman | A61B 1/00082 600/114 |
| 2005/0025646 | A1 | 2/2005 | Miller et al. | |
| 2005/0267330 | A1 | 12/2005 | Deppmeier et al. | |
| 2006/0020165 | A1 | 1/2006 | Adams | |
| 2006/0041186 | A1 | 2/2006 | Vancaillie | |
| 2006/0069306 | A1 | 3/2006 | Banik et al. | |
| 2006/0007427 | A1 | 4/2006 | Friedman et al. | |
| 2006/0074274 | A1 | 4/2006 | Friedman et al. | |
| 2006/0199998 | A1 * | 9/2006 | Akui | A61B 1/00087 600/127 |

(56) References Cited

U.S. PATENT DOCUMENTS

| | | | |
|---|---|---|---|
| 2006/0211916 A1* | 9/2006 | Kasahara | A61B 17/00008 600/114 |
| 2006/0264995 A1 | 11/2006 | Fanton et al. | |
| 2007/0213668 A1 | 9/2007 | Spitz | |
| 2008/0072970 A1 | 3/2008 | Gasser et al. | |
| 2008/0081948 A1 | 4/2008 | Weisenburgh et al. | |
| 2008/0200764 A1 | 8/2008 | Okada | |
| 2008/0242935 A1 | 10/2008 | Inoue | |
| 2008/0262308 A1 | 10/2008 | Prestezog et al. | |
| 2009/0005643 A1* | 1/2009 | Smith | A61B 1/00154 600/125 |
| 2009/0234193 A1 | 9/2009 | Weisenburgh, II et al. | |
| 2009/0244223 A1 | 10/2009 | Mizutani et al. | |
| 2010/0016786 A1 | 1/2010 | Modesitt et al. | |
| 2010/0019786 A1 | 1/2010 | Potok et al. | |
| 2010/0081878 A1* | 4/2010 | Byers | A61B 1/00137 600/125 |
| 2010/0198012 A1 | 8/2010 | Poole et al. | |
| 2010/0198014 A1* | 8/2010 | Poll | A61B 1/00091 600/123 |
| 2011/0208001 A1* | 8/2011 | Haeckl | A61B 1/00071 600/125 |
| 2011/0230716 A1 | 9/2011 | Fujimoto | |
| 2011/0295066 A1 | 12/2011 | Fan | |
| 2012/0178995 A1 | 7/2012 | Newton, IV | |
| 2012/0316394 A1 | 12/2012 | Yoshida et al. | |
| 2013/0205936 A1* | 8/2013 | Schmieding | A61B 1/00066 74/504 |
| 2013/0211433 A1* | 8/2013 | Kadykowski | A61B 17/32 606/159 |
| 2013/0217970 A1 | 8/2013 | Weisenburgh, II et al. | |
| 2013/0289595 A1 | 10/2013 | Edwards et al. | |
| 2014/0364871 A1 | 12/2014 | Kucklick et al. | |
| 2015/0045678 A1 | 2/2015 | Ohzawa et al. | |
| 2015/0087907 A1 | 3/2015 | Konstorum et al. | |
| 2015/0087908 A1 | 3/2015 | Cheng et al. | |
| 2015/0087909 A1 | 3/2015 | Cheng et al. | |
| 2015/0182108 A1 | 7/2015 | Fukuda | |
| 2015/0282695 A1 | 10/2015 | Tay et al. | |
| 2016/0089006 A1 | 3/2016 | Poll et al. | |
| 2016/0095510 A1 | 4/2016 | Oskin et al. | |
| 2016/0220100 A1 | 8/2016 | Cheng et al. | |
| 2018/0192858 A1 | 7/2018 | Konstorum et al. | |
| 2018/0279861 A1 | 10/2018 | Cheng et al. | |
| 2020/0015665 A1 | 1/2020 | Konstorum et al. | |

FOREIGN PATENT DOCUMENTS

| | | |
|---|---|---|
| JP | 62-18101 U | 2/1987 |
| JP | S62-018101 U | 2/1987 |
| JP | H05/038323 A | 2/1993 |
| JP | H06/189893 A | 7/1994 |
| JP | H07308286 A | 11/1995 |
| JP | H08501720 A | 2/1996 |
| JP | 08173370 A | 9/1996 |
| JP | H08-243071 U | 9/1996 |
| JP | H08243071 A | 9/1996 |
| JP | 2005/040184 A | 2/2005 |
| JP | 2007-117289 | 5/2007 |
| JP | 2008289850 A | 12/2008 |
| JP | 2009247797 A | 10/2009 |
| JP | 2012/045325 A | 3/2012 |
| JP | 2012-523855 | 10/2012 |
| JP | 2012254188 A | 12/2012 |
| JP | 2016529032 A | 9/2016 |
| WO | 2002/033296 A2 | 4/2002 |
| WO | 2012/069592 A1 | 5/2012 |
| WO | WO-2015047990 A1 | 4/2015 |
| WO | WO-2015048270 A1 | 4/2015 |

OTHER PUBLICATIONS

International Search report, Application No. PCT/US2014/056911, dated Dec. 12, 2014.
Potentially Related Application, U.S. Appl. No. 14/497,815, dated Sep. 26, 2014.
Potentially Related Application, U.S. Appl. No. 14/493,581, dated Sep. 23, 2014.
Potentially Related Application, U.S. Appl. No. 14/496,473, dated Sep. 25, 2014.
Potentially Related Application, U.S. Appl. No. 14/551,208, dated Nov. 24, 2014.
Potentially Related Application, U.S. Appl. No. 14/551,440, dated Nov. 24, 2014.
Japanese Decision of Rejection from the Japanese Patent Office for Application No. 2016-537951 dated Aug. 28, 2018.
Potentially Related Application, U.S. Appl. No. 14/493,700, filed Sep. 23, 2014, 32 pgs.
"U.S. Appl. No. 14/493,700, 312 Amendment filed Aug. 21, 2018", 5 pgs.
"U.S. Appl. No. 14/493,700, Advisory Action dated Sep. 28, 2017", 3 pgs.
"U.S. Appl. No. 14/493,700, Advisory Action dated Nov. 17, 2016", 3 pgs.
"U.S. Appl. No. 14/493,700, Appeal Decision dated Jul. 11, 2018", 2 pgs.
"U.S. Appl. No. 14/493,700, Examiner Interview Summary dated May 11, 2017", 4 pgs.
"U.S. Appl. No. 14/493,700, Examiner Interview Summary dated May 24, 2018", 4 pgs.
"U.S. Appl. No. 14/493,700, Examiner Interview Summary dated Jun. 27, 2016", 4 pgs.
"U.S. Appl. No. 14/493,700, Final Office Action dated Mar. 21, 2018", 9 pgs.
"U.S. Appl. No. 14/493,700, Final Office Action dated Jun. 15, 2017", 8 pgs.
"U.S. Appl. No. 14/493,700, Final Office Action dated Sep. 7, 2016", 12 pgs.
"U.S. Appl. No. 14/493,700, Non Final Office Action dated Feb. 3, 2017", 10 pgs.
"U.S. Appl. No. 14/493,700, Non Final Office Action dated Mar. 23, 2016", 12 pgs.
"U.S. Appl. No. 14/493,700, Non Final Office Action dated Nov. 16, 2017", 10 pgs.
"U.S. Appl. No. 14/493,700, Notice of Allowance dated Jul. 23, 2018", 7 pgs.
"U.S. Appl. No. 14/493,700, Pre-Appeal Brief filed Jun. 12, 2018", 5 pgs.
"U.S. Appl. No. 14/493,700, PTO Response to Rule 312 Communication dated Sep. 6, 2018", 2 pgs.
"U.S. Appl. No. 14/493,700, Response filed Feb. 15, 2018 to Non Final Office Action dated Nov. 16, 2017", 11 pgs.
"U.S. Appl. No. 14/493,700, Response filed May 3, 2017 to Non Final Office Action dated Feb. 3, 2017", 16 pgs.
"U.S. Appl. No. 14/493,700, Response filed Jun. 23, 2016 to Non Final Office Action dated Mar. 23, 2016", 16 pgs.
"U.S. Appl. No. 14/493,700, Response filed Aug. 15, 2017 to Final Office Action dated Jun. 15, 2017", 11 pgs.
"U.S. Appl. No. 14/493,700, Response filed Oct. 16, 2017 to Advisory Action dated Sep. 28, 2017", 16 pgs.
"U.S. Appl. No. 14/493,700, Response filed Nov. 7, 2016 to Final Office Action dated Sep. 7, 2016", 13 pgs.
"U.S. Appl. No. 14/496,473, 312 Amendment filed Jun. 12, 2018", 4 pgs.
"U.S. Appl. No. 14/496,473, Advisory Action dated Jul. 27, 2017", 3 pgs.
"U.S. Appl. No. 14/496,473, Advisory Action dated Dec. 7, 2016", 3 pgs.
"U.S. Appl. No. 14/496,473, Examiner Interview Summary dated May 3, 2017", 2 pgs.
"U.S. Appl. No. 14/496,473, Final Office Action dated May 11, 2017", 8 pgs.
"U.S. Appl. No. 14/496,473, Final Office Action dated Sep. 13, 2016", 7 pgs.

(56) References Cited

OTHER PUBLICATIONS

"U.S. Appl. No. 14/496,473, Final Office Action dated Dec. 29, 2017", 11 pgs.
"U.S. Appl. No. 14/496,473, Non Final Office Action dated Jan. 17, 2017", 9 pgs.
"U.S. Appl. No. 14/496,473, Non Final Office Action dated Apr. 22, 2016", 9 pgs.
"U.S. Appl. No. 14/496,473, Non Final Office Action dated Aug. 31, 2017", 7 pgs.
"U.S. Appl. No. 14/496,473, Notice of Allowance dated May 23, 2018", 8 pgs.
"U.S. Appl. No. 14/496,473, PTO Response to Rule 312 Communication dated Jun. 22, 2018", 2 pgs.
"U.S. Appl. No. 14/496,473, Response filed Feb. 15, 2018 to Final Office Action dated Dec. 29, 2017", 14 pgs.
"U.S. Appl. No. 14/496,473, Response filed Mar. 24, 2016 to Restriction Requirement dated Mar. 3, 2016", 6 pgs.
"U.S. Appl. No. 14/496,473, Response filed Apr. 17, 2017 to Non Final Office Action dated Jan. 17, 2017", 14 pgs.
"U.S. Appl. No. 14/496,473, Response filed Jul. 7, 2016 to Non Final Office Action dated Apr. 22, 2016", 12 pgs.
"U.S. Appl. No. 14/496,473, Response filed Jul. 11, 2017 to Final Office Action dated May 11, 2017", 13 pgs.
"U.S. Appl. No. 14/496,473, Response filed Nov. 14, 2016 to Final Office Action dated Sep. 13, 2016", 12 pgs.
"U.S. Appl. No. 14/496,473, Response filed Nov. 30, 2017 to Non Final Office Action dated Aug. 31, 2017", 13 pgs.
"U.S. Appl. No. 14/496,473, Restriction Requirement dated Mar. 3, 2016", 6 pgs.
"U.S. Appl. No. 14/497,815, 312 Amendment filed Mar. 28, 2016", 6 pgs.
"U.S. Appl. No. 14/497,815, Examiner Interview Summary dated Feb. 29, 2016", 3 pgs.
"U.S. Appl. No. 14/497,815, Non Final Office Action dated Dec. 21, 2015", 9 pgs.
"U.S. Appl. No. 14/497,815, Notice of Allowance dated Mar. 21, 2016", 9 pgs.
"U.S. Appl. No. 14/497,815, PTO Response to Rule 312 Communication dated Apr. 6, 2016", 2 pgs.
"U.S. Appl. No. 14/497,815, Response filed Feb. 25, 2016 to Non Final Office Action dated Dec. 21, 2015", 11 pgs.
"U.S. Appl. No. 14/497,815, Response filed Dec. 2, 2015 to Restriction Requirement dated Nov. 23, 2015", 4 pgs.
"U.S. Appl. No. 14/497,815, Restriction Requirement dated Nov. 23, 2015", 7 pgs.
"U.S. Appl. No. 15/095,651, 312 Amendment filed Jun. 8, 2018", 7 pgs.
"U.S. Appl. No. 15/095,651, Non Final Office Action dated Jan. 16, 2018", 9 pgs.
"U.S. Appl. No. 15/095,651, Notice of Allowance dated Mar. 30, 2018", 8 pgs.
"U.S. Appl. No. 15/095,651, Preliminary Amendment filed Apr. 11, 2016", 7 pgs.
"U.S. Appl. No. 15/095,651, PTO Response to 312 Communication dated Jun. 2018", 2 pgs.
"U.S. Appl. No. 15/095,651, Response filed Feb. 21, 2018 to Non Final Office Action dated Jan. 16, 2018", 9 pgs.
"U.S. Appl. No. 15/095,651, Response filed Dec. 5, 2017 to Restriction Requirement dated Nov. 14, 2017", 7 pgs.
"U.S. Appl. No. 15/095,651, Restriction Requirement dated Nov. 14, 2017", 6 pgs.
"U.S. Appl. No. 15/917,212, 312 Amendment filed Sep. 24, 2019", 5 pgs.
"U.S. Appl. No. 15/917,212, Corrected Notice of Allowability dated Sep. 4, 2019", 4 pgs.
"U.S. Appl. No. 15/917,212, Examiner Interview Summary dated May 21, 2019", 3 pgs.
"U.S. Appl. No. 15/917,212, Non Final Office Action dated Mar. 26, 2019", 10 pgs.
"U.S. Appl. No. 15/917,212, Notice of Allowance dated Jul. 15, 2019", 7 pgs.
"U.S. Appl. No. 15/917,212, Notice of Non-Compliant Amendment dated Feb. 15, 2019", 3 pgs.
"U.S. Appl. No. 15/917,212, Preliminary Amendment filed Mar. 9, 2018", 6 pgs.
"U.S. Appl. No. 15/917,212, PTO Response to Rule 312 Communication dated Oct. 17, 2019", 2 pgs.
"U.S. Appl. No. 15/917,212, Response filed Jan. 22, 2019 to Restriction Requirement dated Nov. 27, 2018", 7 pgs.
"U.S. Appl. No. 15/917,212, Response filed Feb. 20, 2019 to Notice of Non-Compliant Amendment dated Feb. 15, 2019", 8 pgs.
"U.S. Appl. No. 15/917,212, Response filed May 22, 2019 to Non Final Office Action dated Mar. 26, 2019", 13 pgs.
"U.S. Appl. No. 15/917,212, Restriction Requirement dated Nov. 27, 2018", 6 pgs.
"U.S. Appl. No. 16/002,498, Non Final Office Action dated Nov. 5, 2019", 12 pgs.
"U.S. Appl. No. 16/002,498, Preliminary Amendment filed Jun. 7, 2018", 5 pgs.
"Chinese Application Serial No. 20140047065.X, Office Action dated Sep. 11, 2018", with English translation of claims, 12 pgs.
"Chinese Application Serial No. 201480047065.X, Office Action dated Feb. 28, 2017", with English translation of claims, 13 pgs.
"Chinese Application Serial No. 201480047342.7, Office Action dated Mar. 27, 2017", with English translation of claims.
"Chinese Application Serial No. 201480047342.7, Office Action dated Dec. 14, 2017", with English translation of claims, 10 pgs.
"European Application Serial No. 14777479.8, Communication Pursuant to Article 94(3) EPC dated May 14, 2019", 6 pgs.
"European Application Serial No. 14777479.8, Response filed Sep. 6, 2016", 9 pgs.
"European Application Serial No. 14777479.8, Response filed Sep. 6, 2019 to Communication Pursuant to Article 94(3) EPC dated May 14, 2019", 47 pgs.
"European Application Serial No. 14781019.6, Communication Pursuant to Article 94(3) EPC dated Apr. 24, 2019", 7 pgs.
"European Application Serial No. 14781019.6, Response filed Aug. 23, 2019 to Communication Pursuant to Article 94(3) EPC dated Apr. 24, 2019", 2 pgs.
"European Application Serial No. 14781019.6, Response filed Sep. 7, 2016", 11 pgs.
"International Application Serial No. PCT/US2014/056911, International Preliminary Report on Patentability dated Apr. 7, 2016", 7 pgs.
"International Application Serial No. PCT/US2014/056911, Written Opinion dated Dec. 12, 2014", 5 pgs.
"International Application Serial No. PCT/US2014/057429, International Preliminary Report on Patentability dated Apr. 7, 2016", 10 pgs.
"International Application Serial No. PCT/US2014/057429, International Search Report dated Feb. 19, 2015", 5 pgs.
"International Application Serial No. PCT/US2014/057429, Written Opinion dated Feb. 19, 2015", 8 pgs.
"International Application Serial No. PCT/US2014/057659, International Search Report dated Dec. 23, 2014", 4 pgs.
"Japanese Application Serial No. 2016-537951, Decision in Trial to Reject dated Oct. 23, 2019", with English translation of claims, 34 pgs.
"Japanese Application Serial No. 2016-537951, Office Action dated Jan. 31, 2017", with English translation of claims, 8 pgs.
"Japanese Application Serial No. 2016-537951, Office Action dated May 8, 2018", with English translation of claims, 8 pgs.
"Japanese Application Serial No. 2016-537951, Office Action dated Oct. 3, 2017", with English translation of claims, 9 pgs.
"Japanese Application Serial No. 2016-537952, Office Action dated Jan. 31, 2017", with English translation of claims, 12 pgs.
"Japanese Application Serial No. 2016-537952, Office Action dated Oct. 3, 2017", with English translation of claims, 4 pgs.
"Japanese Application Serial No. 2016-537952, Response filed May 8, 2017 to Written Opinion dated Apr. 28, 2019", with English translation of claims, 24 pgs.

(56) References Cited

OTHER PUBLICATIONS

"Japanese Application Serial No. 2016-537952, Response filed Dec. 21, 2017 to Notice of Reasons for Refusal dated Sep. 27, 2017", with English translation of claims, 11 pgs.

"Japanese Application Serial No. 2016-537952, Written Opinion dated Arp. 28, 2017", with English translation of claims, 19 pgs.

"Japanese Application Serial No. 2016-537952, Written Statement filed May 2, 2017", with English translation of claims, 7 pgs.

"Japanese Application Serial No. 2018-028128, Notice of Reasons for Refusal dated Dec. 28, 2018", with English translation of claims, 6 pgs.

"Japanese Application Serial No. 2018-028128, Written Amendment filed Feb. 20, 2018", with English translation of claims, 4 pgs.

"Japanese Application Serial No. 2018-028128, Written Amendment filed Mar. 14, 2019", with English translation of claims, 2 pgs.

"Japanese Application Serial No. 2019-0878875, Written Amendment filed Jun. 5, 2019", with English translation of claims, 3 pgs.

"U.S. Appl. No. 16/002,498, Notice of Allowance dated Feb. 24, 2020", 7 pgs.

"U.S. Appl. No. 16/002,498, Response filed Feb. 5, 2020 to Non Final Office Action dated Nov. 5, 2019", 11 pgs.

"European Application Serial No. 14777479.8, Communication Pursuant to Article 94(3) EPC dated Dec. 18, 2019", 4 pgs.

"European Application Serial No. 14781019.6, Communication Pursuant to Article 94(3) EPC dated Dec. 18, 2019", 6 pgs.

\* cited by examiner

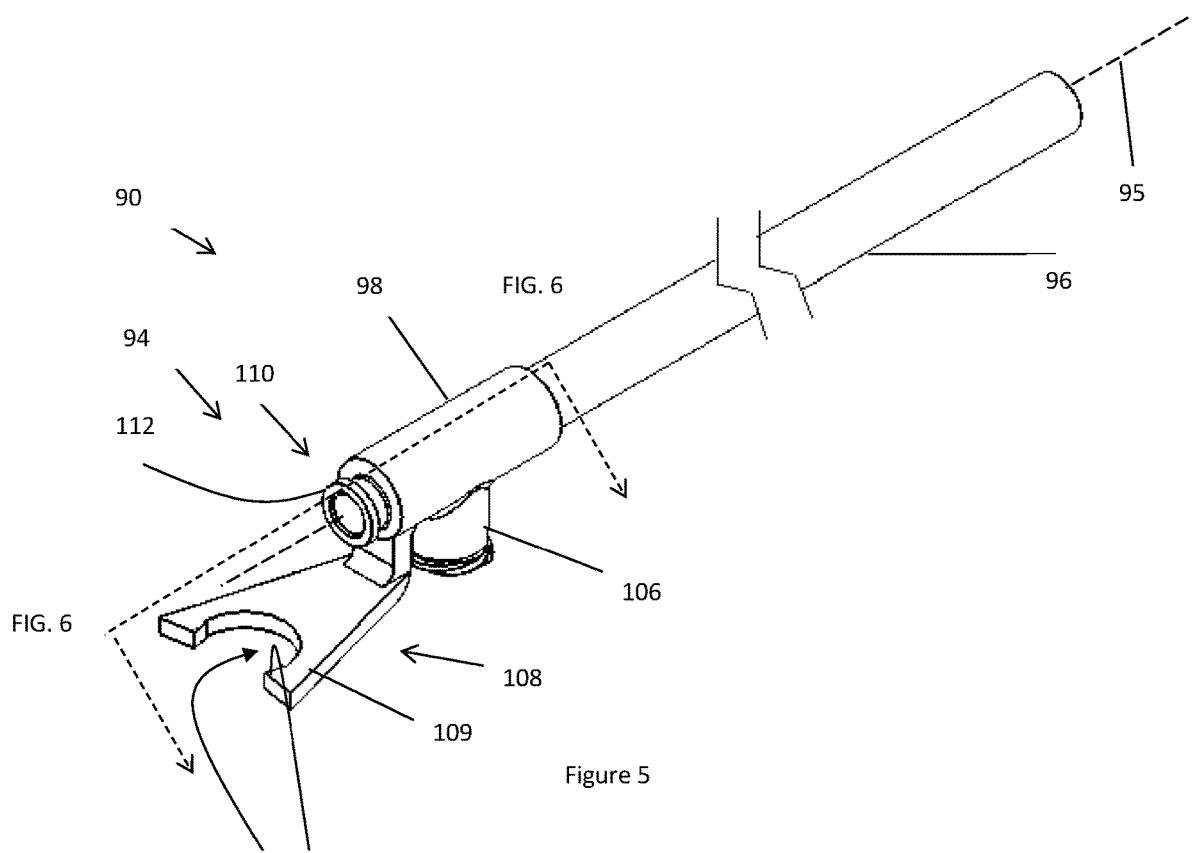
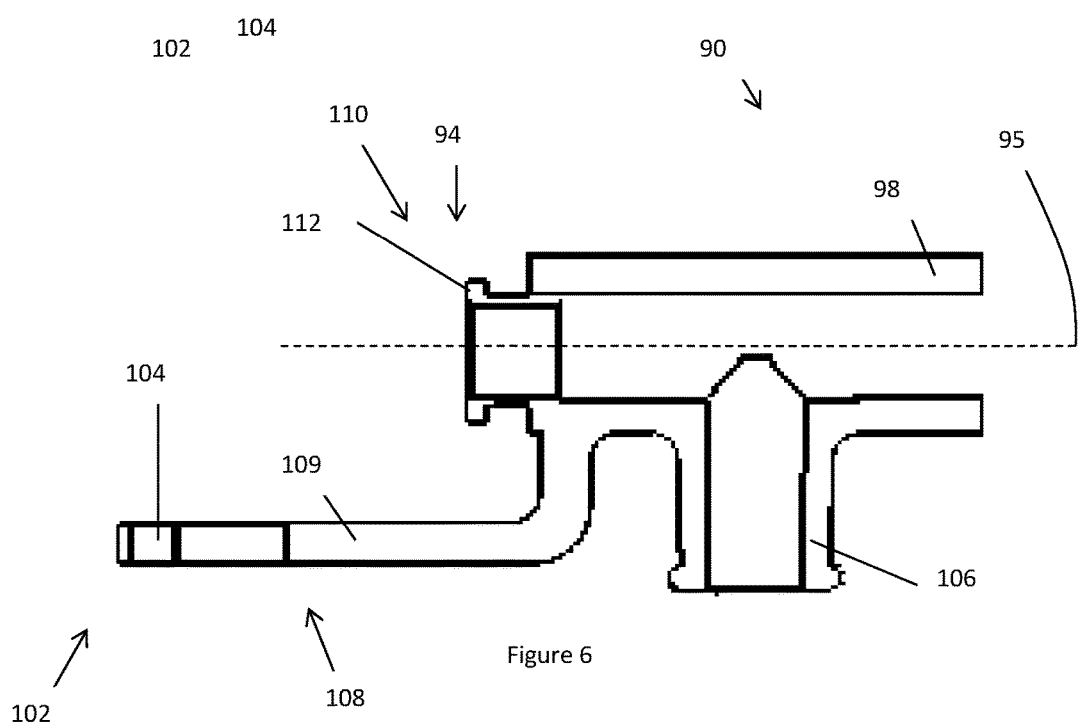

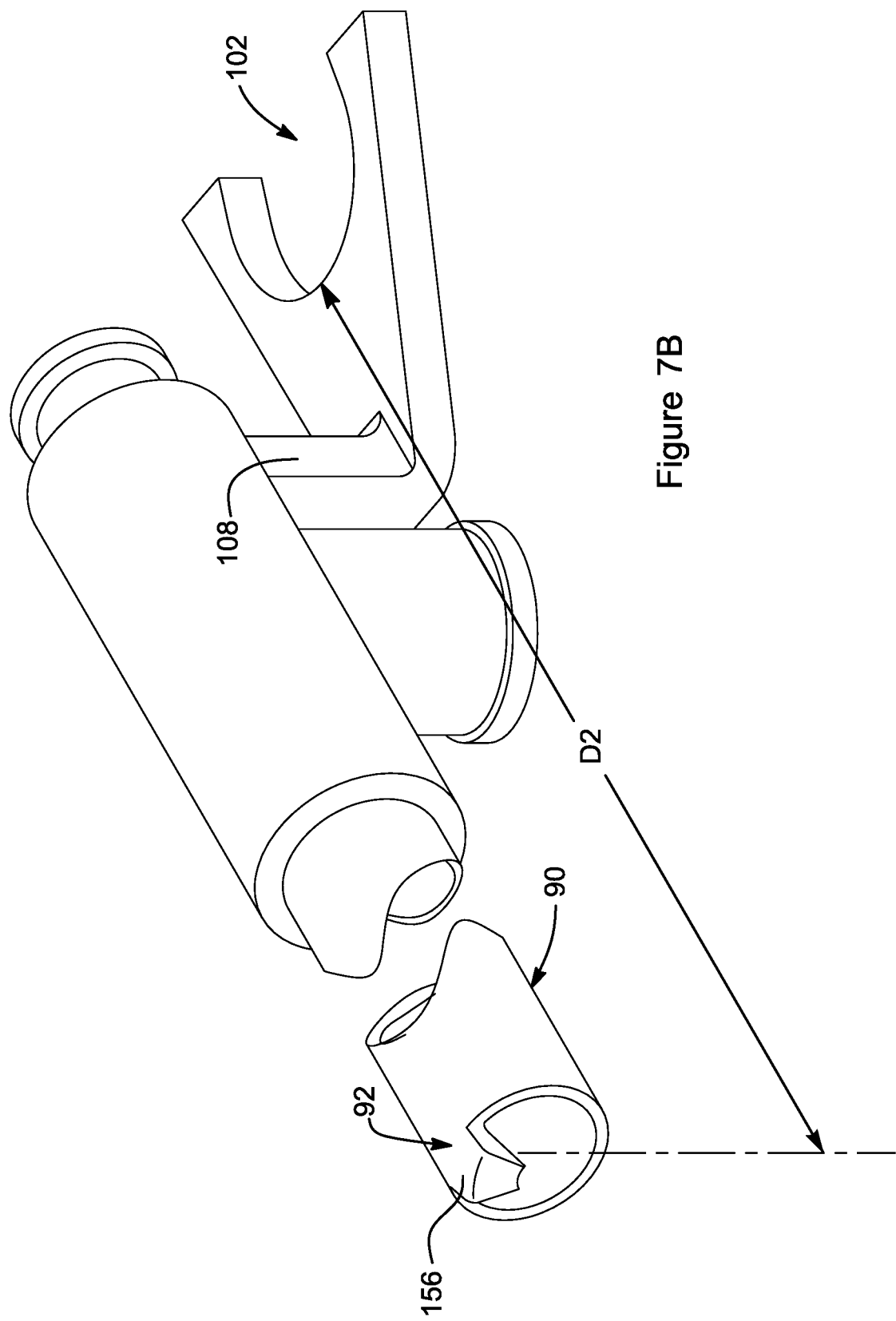

ENDOSCOPE SHEATH ARM

FIELD

The present teachings generally relate to an endoscope sheath that receives all or a portion of an endoscope and more specifically to an arm of an endoscope sheath that is used to locate the endoscope sheath relative to an endoscope.

BACKGROUND

Endoscopes are typically used for minimally invasive surgery or to provide access to an internal location of a patient so that a doctor is provided with visual access. Endoscopes, during use, may be inserted into a location that may include debris that may cover the end of the endoscope and especially cover an imaging device located at the end of the endoscope. For example, an endoscope being used for surgery may become covered by blood and the blood may impair the vision of a surgeon so that surgery becomes increasingly difficult. Attempts have been made to provide various devices to assist a surgeon in clearing the debris from the imaging device of the endoscope and restore vision. These devices may remove some of the debris from the imaging device of the endoscope, however, these devices may not remove all of the debris and/or may leave spots on the imaging device, which may result in continued impairment. Further, movement of the endoscope during use may cause axial or rotational movement of the device relative to the endoscope so that the devices become less effective and/or impairs imaging using the imaging device.

Examples of some endoscope cleaning devices may be found in U.S. Pat. Nos. 4,646,722; 5,170,774; 5,419,309; 5,575,756; 6,110,103; 6,126,592; 6,447,446; and 7,811,228, all of which are incorporated by reference in their entirety herein for all purposes. It would be attractive to have an endoscope sheath having an arm that aligns a tip of an endoscope sheath with endoscope tips of various viewing angles. It would be attractive to have an endoscope sheath that directs fluid and/or suction across a distal end of the endoscope so that debris and other imagine blocking substances are removed from the distal tip of the endoscope. It would be attractive to have an endoscope sheath with an alignment device (i.e., an arm) that rotationally and axially immobilizes the endoscope sheath with regard to the endoscope. What is needed is an endoscope sheath that is configured to receive fluid, suction, one or more functional devices, or a combination thereof so that the fluid, suction, one or more functional devices, or a combination thereof that extend from a proximal end to a distal end.

SUMMARY

The present teachings meet one or more of the present needs by providing: an endoscope sheath comprising: (a) a tube configured to receive all or a portion of a shaft of an endoscope, the endoscope including a light post in a proximal end region of the endoscope; and (b) an arm attached to and extending from a proximal end region of the sheath; wherein the arm has one or more features that are in communication with the light post to orient the sheath axially and rotationally with respect to the endoscope.

Another possible embodiment of the present teachings comprises: an endoscope sheath comprising: a tube configured to receive all or a portion of an endoscope having: a distal end, a proximal end, a shaft having a cylindrical body, a light post extending from a proximal end region of the endoscope; and an arm attached to and extending from a proximal end region of the sheath; wherein the arm has a socket with an undercut that is configured to secure the endoscope sheath to the light post and prevent axial movement of the sheath towards the proximal end and the distal end with respect to the endoscope.

The teachings herein provide an endoscope sheath having an arm that aligns a tip of an endoscope sheath with endoscope tips of various angles. The teachings provide an endoscope sheath that directs fluid and/or suction across a distal end of the endoscope so that debris and other imagine blocking substances are removed from the distal tip of the endoscope. The teachings provide an endoscope sheath with an arm that rotationally and axially immobilizes the endoscope sheath with regard to the endoscope. The teachings provide an endoscope sheath that is configured to receive fluid, suction, one or more functional devices, or a combination thereof so that the fluid, suction, one or more functional devices, or a combination thereof extend from a proximal end to a distal end.

BRIEF DESCRIPTION OF THE DRAWINGS

FIG. 5 illustrates a perspective view of an endoscope sheath and arm;

FIG. 6 illustrates a cross-sectional view of an arm extending from an endoscope sheath;

FIG. 7B illustrates a side view of another example of an endoscope sheath including an arm;

DETAILED DESCRIPTION

Figure 1A:
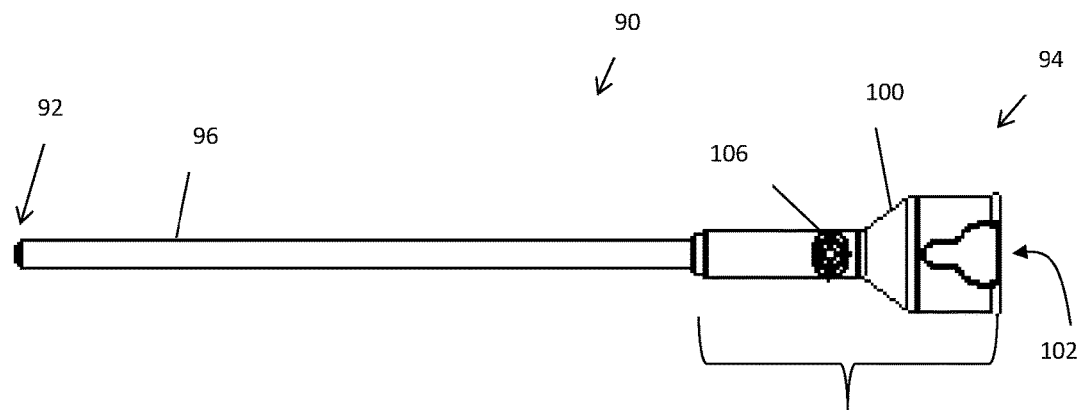
FIG. 1A illustrates a top view of an endoscope sheath.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application Ser. No. 61/882,652, filed on Sep. 26, 2013, the contents of which are both incorporated by reference herein in their entirety for all reasons. The present teachings provide an endoscope sheath for use in a system 2. The system of the teachings herein includes an irrigation source 4 and a suction source 10 that are both connected to an endoscope sheath 90 that is in communication with an endoscope 60. The system 2 may include one or more control modules 30. The system 2 may function to dean an endoscope. Preferably, the system 2 functions to clean a distal tip 62 of an endoscope 60. More preferably, the system 2 functions to clean an imaging device of an endoscope. The system 2 may include one or more functional components that may extend proximate to a distal end 62 of an endoscope 60 or beyond a distal end 62 of an endoscope 60. The system 2 may provide one or more conduits relative to the endoscope 60. The system 9 may protect the endoscope 60. The system 2 may include one or more sources of irrigation fluid 4 for use with the system 2 and the one or more sources of irrigation fluid, suction, or both may be controlled by one or more control modules 30.

The one or more control modules 30 may function to control the amount of fluid, suction or both applied to a predetermined area, an area of interest, the endoscope, or a combination thereof. The one or more control modules 30 may be powered by electricity, battery powered, or both. The one or more control modules 30 may include one or more pumps 14, one or more valves 8, one or more user interfaces 31, or a combination thereof. The one or more user interfaces 31 may be one or more control knobs, one or more selectors, one or more indicators, one or more user controls, one or more devices for changing a parameter, or a combination thereof. The one or more control modules 30 may include any of the pumps 14 discussed herein and based upon feedback from the user interface 31 may control the pump 14 to perform the selected parameter. The control module 30 may include a microprocessor, a computer, a control algorithm, or a combination thereof. The control module 30 may control one more valves 8 located within the system 2, connected to the control module 30, or both. The one or more control modules 30 may perform a suction function, an irrigation function, or a combination of both upon a selection by the user as is indicated by the user interface 31. The control module 30 may control the running speed, pumping duration, or both of the pump 14 so that irrigation fluid is moved to the sheath 90.

The irrigation fluid may function to clean an endoscope 60, irrigate a surgical site, clear debris from a location proximate to the endoscope, be bioabsorbable, or a combination thereof. The irrigation fluid may function to move solid particles, move opaque fluids, or both. The irrigation fluid may be applied with a pressure. The pressure of the irrigation fluid may be varied by changing the height of the irrigation source relative to the sheath 90 so that the head of the irrigation fluid is increased or decreased. The irrigation fluid may be applied with a pressure of about 0.10 MPa or more, about 0.20 MPa or more, about 0.30 MPa or more, or even about 0.50 MPa or more. The irrigation fluid may be applied with a pressure of about 3 MPa or less, about 2 MPa or less, about 1 MPa or less, or even about 0.75 MPa or less. The irrigation fluid may be applied with a sufficient amount of pressure that the surface tension of the irrigation fluid wicks the irrigation fluid across the distal end 62, the imaging portion, or both of the endoscope 60 (e.g., the pressure may be low enough that the irrigation fluid remains in contact with the endoscope, the sheath, or both). The irrigation fluid may be applied with a gravity feed, thus, the pressure of the irrigation fluid may be determined by the height of an irrigation source. For example, the irrigation source may be an IV bag and the height of the IV bag may determine the amount of pressure and/or force generated at the distal tip of the sheath, endoscope, or both. The irrigation fluid may be applied by a pump 14 that pumps the fluid at a predetermined pressure. The irrigation fluid may be continuously applied, intermittently applied, or both during an application cycle. The pressure of the irrigation fluid may change when the irrigation fluid reaches the end of an endoscope sheath 90 so that the fluid cleans the endoscope 60, creates turbulence at the end of the endoscope 60, or both. Preferably, the pressure is sufficiently low so that the flow across the endoscope 60 is laminar. The pressure of the irrigation fluid may be varied based upon the size, length, or both of an irrigation line 6 extending between an irrigation source 4 and the sheath 90. The irrigation source 4 may be a reservoir that fluid is drawn from by a fluid movement mechanism (e.g., a pump 14) and moved through the sheath 90 to provide irrigation to a distal end 62 of an endoscope 60, to clean an endoscope, or both.

The pump 14 may function to circulate irrigation fluid, move irrigation fluid through one or more lines 6, move fluid through a sheath 90, or a combination thereof. The pump 14 may function to create a negative pressure (e.g., suction or vacuum). The pump 14 may move fluid with an impeller. The pump 14 may be a lobe pump, a centrifugal pump, a positive displacement pump, a rotary positive displacement pump, a diaphragm pump, peristaltic pump, rope pump, a gear pump, a screw pump, a progressing cavity pump, a roots-type pump, a plunger pump, or a combination thereof. Preferably, the pump 14 moves a constant amount of fluid upon being activated, a constant amount of fluid may be varied from application to application, or both. More preferably, the pump 14 is a peristaltic pump. The peristaltic pump may provide irrigation fluid a point of interest and preferably to a distal end 62 of an endoscope 60 within a surgical site.

The one or more irrigation lines 6 may function to connect the sheath 90 to an irrigation source 4. The irrigation line 6 may function to create a head so that the irrigation fluid is applied with a pressure. The irrigation line 6 may be flexible, movable, or both. The irrigation line 6 may be made of any material that is compatible with the irrigation fluid, a patient, use in a surgical procedure, or a combination thereof. The irrigation line 6 may connect the sheath 90 to an irrigation source 4, a suction source 10, or both (i.e., suction may be applied through the irrigation line 6).

The suction source 10 may function to remove fluid, debris, opaque fluids, unwanted material, or a combination thereof from a point of interest, from a distal end 92 of the sheath 90, a distal end 62 of the endoscope 60, or a combination thereof. The suction source 10 may function to perform a drying function, remove fluid spots, fluid droplets, or a combination thereof. The suction source 10 may be a pump, reversal of a motor, a common suction source, a hospital suction source, or a combination thereof. The suction source 10 may apply a sufficient amount of vacuum to remove a predetermined amount of fluid in a predetermined amount of time. For example, the suction source 10 may apply suction so that 10 ml of fluid may be removed in 1 to 2 seconds. The suction source 10 may apply continuous suction, intermittent suction, or both.

The suction line 12 may function to connect to the sheath 90 so that suction may be pulled through the sheath 90. The suction line 12 may function to connect the sheath 90 to a suction source 10. The suction line 12 may assist is moving fluids, removing fluids, removing debris, removing opaque fluids, removing particles, or a combination thereof. The suction line 12 may be any line that may assist in creating a vacuum at a distal tip of the endoscope 60, the sheath 90, or both. The suction line 6 and the irrigation line 12 may be the same line. The suction line 12 and the irrigation line 6 may be connected to a common line 18. The suction line 12 and the irrigation line 6 may be connected by one or more fittings, one or more valves or both.

The one or more valves 8 may function to allow only one function to work at a time (e.g., irrigation or suction). The one or more valves 8 may function to block the irrigation line 6, the suction line 12, or both. The one or more valves 8 may only allow suction or irrigation to be applied at a given time. The one or more valves 8 may be a check valve, a back flow preventer, a pinch valve, or a combination thereof. The one or more valves 8 may be located proximate to the sheath 90, proximate to the irrigation source 4, proximate to the suction source 10, or a location therebetween. Each of the lines may include a valve 8. If more than one valve is present the valves may be electrically connected, hydraulically connected, fluidly connected, or a combination thereof so that if one valve is opened another valve is closed. The two or more valves (e.g., a first valve and a second valve) may be electrically connected, electrically controlled, or both. The two or more valves may be operated in a sequence (e.g., one opened and then one closed), operated simultaneously, operated on a delay, or a combination thereof. For example, only one valve may be open at a time. In another example, one may close and after a time delay another may open. The one or more valves 8 may be part of a common fitting 16, located proximate to a common fitting, or both.

The one or more common fittings 16 may function to connect two or more lines into a common line 18. The one or more common fittings 16 may function to connect a suction line 12 and an irrigation line 6 to a common port. The one or more common fittings 16 may connect a single line to multiple devices so that multiple devices may be used simultaneously, in series, in parallel, or a combination thereof. For example, the common fitting 16 may connect a suction line 12 and an irrigation line 6 to a common line 18 that is connected to a sheath 90 and during operation an irrigation fluid may be applied and then after a delay and/or immediately when the irrigation fluid ceases to be applied, suction may be applied to the suction line so that irrigation fluid, excess irrigation fluid, debris, particles, opaque fluids, or a combination thereof are removed from the distal end 62 of the endoscope 60. The one or more common fittings 16 may have two or more openings, three or more openings, four or more openings, or even five or more openings. Each opening may receive at least one line and fluidly connect the one or more lines together. More than one common fitting may be used to connect multiple lines together. For example, a first common fitting 16 with three openings may be connected to another common line 18 with three openings so that two tubes are connected to one opening of a common fitting and one tube is connected to each of the other two openings. Preferably, the common fitting 16 is generally "Y" shaped and two of the openings lead into a third opening that is connected to a common line 18 and/or a delivery line 42.

The common line 18 may function to deliver irrigation fluid, suction, or both to a sheath 90. The common line 18 may function to provide a combination of multiple different fluids, devices, suction level, fluid pressures, or a combination thereof. The common line 18 may provide a single access point between the irrigation source 4, the suction source 10, or both and the sheath 90. The common line 18 may have an increased cross-sectional area (e.g., diameter) relative to the cross-sectional area of the irrigation line 6, the suction line 12, or both. The common line 18 may be the same size as one or both of the irrigation line 6, the suction line 12, or both. The common line 18 may extend between the common fitting 16 and a port 106 of the sheath 90. The common line 18 may be a delivery line 42.

The delivery line 42 may function to deliver fluids to a sheath 90. The delivery line 42 may function to deliver suction to the sheath 90. The delivery line 42 and the common line 18 are preferably the same line. The delivery line 42, common line 18, or both may be used during an application cycle.

The application cycle may be any cycle where an endoscope is cleaned. The application cycle may be a cycle where a combination of different items are applied. The application cycle may be a cycle where an irrigation fluid and suction are applied in a sequence to clean an endoscope 60. The application cycle may be a combination of one or more applications of fluid, one or more applications of suction, or both. The application cycle may be an application of fluid an immediately thereafter an application of suction to remove excess fluid form a point of interest, the distal end 62 of the endoscope 60, the distal end 92 of the sheath 90, or a combination thereof. The application cycle may have no delay between an end of the application of an irrigation fluid and the beginning of the application of suction. For example, upon completion of the irrigation fluid being applied the suction may immediately begin. The application cycle may be varied by a user. The application cycle may include only an application of fluid (i.e., a flushing cycle, a washing manner) with no suction. The application cycle may be user activated for a predetermined amount of time. The application cycle may be activated based upon a duration a user activates a switch. For example, a user may pre-set the activation cycle so that one touch of the switch causes the irrigation fluid to run for 5 seconds. The user may pre-set the activation cycle so that no suction is used. The application cycle may concurrent application of fluid and suction. For example, suction may begin being applied before the irrigation fluid is turned off. The application cycle of the irrigation fluid, the suction, or both may be changed by a user changing a selector, actuating a control longer, changing an input, or a combination thereof. The application cycle may be sufficiently long so that an image sensor of an endoscope 60 is clear and good images may be taken.

The endoscope 60 may function to provide an image to a surgeon, a doctor, a mechanic, a technician, a nurse, any other person who desires visual access to a remote location, or a combination thereof. The endoscope 60 may be used for non-invasive surgery. The endoscope may be used for orthoscopic surgery. The endoscope 60 may be used for insertion into an orifice including an ear, nose, throat, rectum, urethra, or a combination thereof. The endoscope 60 may have a generally circular cross-section. The endoscope 60 may have a tubular section that is generally cylindrical. The endoscope 60 may have a tubular section extending to the distal end 62 and a handpiece connected to the tube and extending to the proximal end 64. The endoscope 60 may include one or more image sensors in a distal end region. The endoscope 60 may include two or more image sensors. The endoscope may include an image sensor at the most distal point of the endoscope 60. The endoscope 60 may include an image sensor that is located on an angle. The angle of the image sensor may be about 0°, 20°, 30°, 45°, 60°, 70°, or a combination thereof. The image sensor may provide black and white images, color images, thermal images, or a combination thereof. Preferably, the image sensor, imaging device, or both are located substantially at the distal end 62. The angle of the image sensor, the viewing face, or both may dictate the angle, shape, viewing cone 78, or a combination thereof of the endoscope 60.

The viewing cone 78 may be an area that of visibility of the endoscope 60. The viewing cone 78 may be variable, adjustable, or both. The angle of the viewing cone 78 may be movable. The angle of the viewing cone 78 may be predetermined based upon the type of endoscope selected. The angle of the viewing cone 78 may not be affected by the flow director 158, lumen 168, sheath 90, or a combination thereof. The viewing cone 78 may extend outward from the distal end 62 of the endoscope 60 in a cone shape.

The distal end 62 of the endoscope 60 may function to be inserted into a patient so that a feature of interest may be viewed through minimally invasive means. The distal end 62 of the endoscope 60 may be the leading portion of the endoscope 60 (i.e., the first portion hat enters a patient). The distal end 62 may function to provide washing functions, suction functions, irrigating functions, or a combination thereof that directs irrigation fluid and/or suction across the viewing face of the endoscope, the lens, or both. The distal end 62 of the endoscope 60 may be on an opposing end of the endoscope 60 as a proximal end 64. The proximal end 64 may function to be gripped by a user. The proximal end 64 may function to provide controls to a user. The proximal end 64 may provide an interface for connecting other functional components such as an imaging device (e.g., a camera). The proximal end 64 may function to provide power, sensing, suction, fluid, control, or a combination thereof to the distal end 62 of the endoscope 60. The proximal end 64 may be retained out of the patient and the distal end 62 may be inserted in the patient. A shoulder 70 may be located between the distal end 62 and the proximal end 64.

The shoulder 70 may function to prevent the proximal end 64 from entering a patient. The shoulder 70 may function to form a connection point with a tube of the endoscope 60. The shoulder 70 may be a terminal portion of a proximal end 64 of the endoscope 60. The shoulder 70 may prevent a sheath 90 from axially moving towards the proximal end 64 of the endoscope 60. The shoulder 70 may be a distal end of the proximal end portion of the endoscope 60. The shoulder 70 may be generally vertical, generally flat, generally orthogonal to the longitudinal axis 95 of the tubular section of the sheath 90, or a combination thereof. One or more light posts 72 may be located in a distal end region of the endoscope 60 in a proximal direction relative to the shoulder 70 (e.g., closer to the shoulder end then a visual port 74 end).

The light post 72 may function to provide light into the endoscope 60. The light post 72 may direct light into the endoscope 60 and out of the tube of the endoscope 60 so that a feature of interest is illuminated. The light post 72 may provide light so that a user can see features of interests that are located in low light conditions. The light post 72 may be rigid. The light post 72 may be immobile and/or fixedly connected to the endoscope 60 so that the light post 72 has a fixed position on the endoscope 60. The light post 72 may be made of metal. The light post 72 may be integral with a main portion of the proximal end 64. The light post 72 may be made of metal or some other biocompatible material. The one or more light posts 72 may assist in providing light through the endoscope 60, so that the visual port 74 may be used for observing a feature of interest at a distal end 62 of the endoscope 60.

The visual port 74 may function to provide a viewing window for a user. The visual port 74 may function to allow a user to observe a feature of interest. The visual port 74 may function to provide an output so that an image is displayed on a monitor. The visual port 74 may provide visual access through the endoscope 60 to a user. The visual port 74 may provide a connection point to a camera that displays the image on a larger image device such as a television or a monitor. The visual port 74 may be an optical window at the proximal end 64 that provides visual access to a viewing lens 76 at the distal end 62.

The viewing lens 76 may function to provide a window that an image sensor views through. The viewing lens 76 may be a cover over an image sensor. The viewing lens 76 may have a cross-sectional length (e.g., diameter) that is less than the cross-sectional length of the endoscope 60. The viewing lens 76 may have a largest dimension that is larger than the cross-sectional thickness of the endoscope 60. For example, when the endoscope 60 has an imaging device at a 70° angle the viewing lens 76 may be greater than the cross-sectional length of the endoscope 60. The viewing lens 76 may protect the imaging device (e.g., camera) from fluid, damage, corrosion, or a combination thereof. The viewing lens 76 may cover one or more imaging devices or even two or more imaging devices. The viewing lens 76 when in use may become covered with debris, fluid, blood, opaque fluids, or a combination thereof. The viewing lens 76 may be inhibited from allowing a clear image, an undistorted image, or both to be formed. The viewing lens 76 may be partially of fully covered by a sheath 90, be partially or fully surrounded by a sheath 90, or both. Preferably, the sheath 90 is located proximate to the viewing lens 76 without interfering with the range of vision created by the viewing lens 76.

The sheath 90 may function to provide one or more conduits for a fluid, suction, a functional device, or a combination thereof to extend out of a distal end region. The sheath 90 may provide a conduit that extends from a proximal end 94 to a distal end 92. The sheath 90 may be open at both ends. The sheath 90 may be open at the distal end 92 and the proximal end 94 so that an endoscope 60 may be inserted into the proximal end 94 and extend through the sheath 90 and view a feature of interested located near the distal end 92. The distal end 92 of the sheath 90 may have a stop that located the distal end 62 of the endoscope 60 relative to the distal end 92 of the sheath 90. The sheath 90 may include one or more lumen 170, create one or more lumen 170, or both. The sheath 90 may include one or more parts that when connected together create a conduit that provides irrigation fluid, suction, or both to a distal end 62 of the endoscope 60. The sheath 90 may substantially mirror the shape of the endoscope 60. Thus, for example, if the endoscope 60 has a circular cross-section then then sheath 90 has a circular cross section. The sheath 90 may function as an endoscope cleaner. The sheath 90 may have a distal end 92 and a proximal end 94 with a longitudinal axis 95 that extends therebetween.

The distal end 92 of the sheath 90 may function to direct irrigation fluid, suction, or both across the viewing lens 76 of the endoscope 60. The distal end 92 may function to open, be open, or both so that irrigation fluid may exit the sheath 90. The distal end region may include one or more annular gaps (e.g., ring shaped gaps). The distal end 92 may function to not interfere with the imaging capabilities of the endoscope 90. The distal end 92 may open out so that velocity of the irrigation fluid drops as the irrigation fluid reaches the distal end 92. The distal end 92 may include one or more distal end locating features. The distal end locating features may include a hooking portion 156, a projecting portion 154, or both. The hooking portion 156, the projecting portion 154 or both may extend from the distal end 92 of the sheath 90. The hooking portion 156 may extend out from the distal end 92 and down towards an opening in the sheath 90. The hooking portion 156 may extend in a direction so that irrigation fluid as it exits the sheath 90 is directed across the distal end 62 of the endoscope 60. The hooking portion 156 may extend at an angle, in an arcuate manner, have one or more linear segments connected by an angular portion, or a combination thereof. The hooking portion 156 may have a tapered tip. The hooking portion 156 may extend generally downward from the distal end 92. The distal end 92 may include a projecting portion 154 that functions to direct irrigation fluid downward, across a viewing lens 76 of the endoscope 60, or both. The projecting portion 154 may be linear along its entire length. The projecting portion 154 may have a tapered tip portion. The projecting portion 154, the hooking portion 156, or both may extend axially away from the proximal end 94 of the sheath 90.

The proximal end 94 of the sheath 90 may function to create a connection with the endoscope 60. The proximal end 94 may align the sheath 90 relative to the endoscope 60. The proximal end 94 of the sheath 90 may axially align the sheath 90 relative to the endoscope 90, radially align the sheath 90 relative to the endoscope 60, axially align the distal ends 62,92 of the sheath 90 and the endoscope 60, the sheath 90 axially relative to a light post 72 of the endoscope 60, the sheath 90 rotationally relative to a light post 72 of the endoscope 60, or a combination thereof. The proximal end 94 may receive all or a portion of the endoscope 60. The proximal end 94 may contact a shoulder 70 of the endoscope 60. A longitudinal axis 95 may extend between the proximal end 94 and the distal end 92 of the sheath 90. The longitudinal axis 95 may extend through a through hole 152 that extends the length of the sheath 90. The endoscope 60 may extend within the sheath 90 along the longitudinal axis 95. The longitudinal axis 95 may extend from a connection point between the endoscope 60 and the sheath 90 and through a tube 96 of the sheath 90.

The tube 96 may function to receive the imaging device of the endoscope 60. The tube 96 may be located at the distal end 62 of the endoscope 60. The tube 96 may be generally the same size and shape as the endoscope 60. For example, if the endoscope 60 has a generally circular cross-section then the tube 96 may have a generally circular cross-section. The tube 96 may have a shape that is different than the endoscope 60. The tube 96 may be any shape so that the tube 96 is configured to receive the endoscope 60. The tube 96 may be connected to: a hub 98, integrally formed with a hub 98, in fluid communication with a port 106, connected to a port 106, include a through hole 152 that is in communication with a port 106, or a combination thereof. The tube 96 may be connected to a handpiece at the proximal end 94. The tube 96 may be integrally formed with a handpiece. The tube 96 may have a uniform wall thickness, a variable wall thickness, or both. The wall thickness may vary along the length of the tube 96. The wall thickness may vary along the circumference of the tube 96. For example, the tube 96 may have a wall that is twice as thick on a bottom half of the tube than a top half of a tube 96 when viewing the tube 96 in a cross-section. The tube 96 may include one or more positioning devices along its length. The one or more positioning devices may be one or more dimples 134. The tube 96 may be any shape so that the tube 96 is configured to receive the endoscope 60. The tube 96 may be connected to a hub 98, integrally formed with a hub 98, in fluid communication with a port 106, connected to a port 106, include a through hole 152 that is in communication with a port 106, or a combination thereof.

The port 106 may function to provide access into the tube 96 of the sheath 90. The port 106 may function to provide a fluid connection, a suction connection with one or more irrigation sources, one or more suction sources, one or more common lines 18, one or more delivery lines 42, or a combination thereof. The port 106 may form a fixed connection with one or more lines so that suction, irrigation fluid, or both may be provided through the port 106. The port 106 may provide direct access to the inside of the tube 96. The port 106 may be configured so that one or more functional elements (e.g., a cutting tool, a cauterizing tool, or both) may gain access to the inside of the tube 96 of the sheath 90, may extend out of the distal end 92 of the sheath 90, or both. For example, the port 106 may receive items that do not flow. The port 106 may be part of the tube 96, the hub 98, or both.

The hub 98 may function to connect the sheath 90 to the endoscope 60. The hub 98 may function to seal the sheath 90 to the endoscope 60. The hub 98 may surround a portion of the endoscope 60. The hub 98 may function to create a fluid seal with the endoscope 60 so that the irrigation fluid, suction, or both do not leak. The hub 98 may receive a shoulder 70 of the endoscope 60 so that the shoulder 70 and the hub 98 form a fluidly sealed connection. The hub 98 may have a circular cross section. The hub 98 may taper as it extends towards the distal end 92 of the sheath 90. The hub 98 may be large enough to receive all or a portion of the endoscope 60. The hub 98 may partially extend around the endoscope 60, fully extend around the endoscope 60, or a combination of both. The hub 98 may have a thicker section that connects to the tube 96. The hub 98 may be fastened to the tube 96. The hub 98 may be connected to the tube 96 by a mechanical fastener such as threads, a snap, a one way connection system, a series of ribs, or a combination thereof. The hub 98 may connect to the tube 96 by one or more adhesives. The hub 98 may include a collar 100, an arm 108, or both that receive all or a portion of the endoscope 60.

The collar 100 and the arm 108 may perform the same functions. The collar 100 and the arm 108 may include the same elements. The collar 100 may be an integral part of the hub 98. The collar 100 may form a majority of the hub 98 (e.g., 50 percent or more, 60 percent or more, or 70 percent or more). The collar 100 may function to prevent rotational movement. The collar 100 may function to prevent axial movement. The collar 100 may function to receive all or a portion of the endoscope 60. The collar 100 may function to receive a light post 72 of the endoscope 60. The collar 100 may surround the light post 72. The collar 100 may extend partially around the light post 72. The collar 100 may include a socket 102 that receives all or a portion of the light post 72.

The socket 102 may function to contact the light post 72 so that the sheath 90 and endoscope 60 are axially aligned, rotationally aligned, or both. The socket 102 may function to receive all or a portion of the endoscope 60. The socket 102 may receive all or a portion of the light post 72 without locking the sheath 90 to the light post 72. The socket 102 may function to lock the sheath 90 to the endoscope 60. The socket 102 may function to rotationally lock the sheath 90 to the endoscope 60, axially lock the sheath 90 to the endoscope 60, or both. The socket 102 may prevent all axial movement of the sheath 90 relative to the endoscope 60. For example, the socket 102 may prevent axial movement of the sheath 90 in the proximal direction 94 and the distal direction 92 relative to the endoscope 60, light post 72, the distal end 62 of the of the endoscope 60, or a combination thereof. The socket 102 once connected to the light post 72 may constrain all axial movement of the sheath 90 so that the distal end 92 of the sheath 90 and the distal end 62 of the endoscope 60 are axially aligned. The socket 102 may be a positive feature that forms a connection with the endoscope 60. The socket 102 may be a negative feature, an absence of material, a lack of material, a section free of material, or a combination thereof. The socket 102 may include an opening that receives all or a portion of an endoscope 60 and preferably receives a light post 72 of an endoscope 60. The socket 102 may be part of the collar 100, the arm 108, or both. The size of the opening in the socket 102 may be variable in size so that the socket 102 may be able accommodate endoscopes 60, light posts 72, or both of different sizes. The socket 102 may have an opening that is semicircular, rectangular, "V" shaped, hexagonal, a geometric shape, or a combination thereof that is configured to receive a light post 72 or another component of the endoscope 60. The socket 102 may include a hinge that allows for the socket size to be varied. The material characteristics of the socket 102 may allow for the socket size, the opening in the socket, or both to be varied. The material of the socket 102 may be elastically deformable so that the socket 102 receives the light post 72 and forms an interference fit with the light post 72. The socket 102 may mirror the shape of one or more portions of the endoscope 60. The socket 102 may mirror the shape of the light post 72. The socket 102 may extend partially and/or fully around the light post 72. The socket 102 may include one or more fingers 109 that extend around an opening in the socket 102. The socket 102 may include one or more fingers 109 with one or more undercuts 104.

The one or more fingers 109 may function to extend around an opening. The one or more fingers 109 may create an opening between adjacent fingers. The one or more fingers 109 may function to be movable during attachment. The one or more fingers 109 may function to form an interference fit. The one or more fingers 109 may function to prevent rotational movement, axial movement, or both of the sheath 90. The one or more fingers 109 may be elastically deformable. The one or more fingers 109 may be laterally translatable (e.g., extend within their own plane). The one or more fingers 109 may create a gripping force on the endoscope 60, the light post 72, or both. The one or more fingers 109 may each form a gripping force of about 2 N or more, about 5 N or more, about 7 N or more, or even about 10 N or more. The one or more fingers 109 may each include one or more undercuts 104 and may move the one or more undercuts 104 into contact with a light post 72, around a light post 72, or both.

The one or more undercuts 104 may prevent axial movement, rotational movement, or both. Preferably, the one or more undercuts 104 may prevent axial movement towards the distal end 62, 92 of the endoscope 60, the sheath 90, or both. The undercuts 104 and a distal end of the socket 102 may work in conjunction to constrain axial movement (e.g., both proximally and distally) of the sheath 90 relative to the endoscope 60. The one or more undercuts 104 may assist in forming a fixed connection with the endoscope 60, form a fixed connection with the endoscope 60, or both. The one or more undercuts 104 may grip a portion of the endoscope 60. Preferably, the undercuts 104 extend at least partially around the endoscope 60 or a portion of the endoscope 60 so that the endoscope 60 and sheath 90 are fixedly connected. More preferably, the undercuts 104 extends at least partially around the light post 72 of the endoscope 60 or into a portion of the light post 72 to form a fixed connection. The one or more undercuts 104 may form an interference fit, a friction fit, a snap fit, or a combination thereof with the endoscope 60 and preferably with the light post 72 of the endoscope 60. The one or more undercuts 104 may be two opposing undercuts that are located on opposing fingers 109 of the socket 102. The undercuts 104 may angle towards each other, extend towards an inside of the socket 102, reduce the diameter of the socket 102, or both. The undercuts 104, the socket 102, the fingers 109, or a combination there of may be part of a collar 100, a hub 98, an arm 108, or a combination thereof.

The arm 108 may function to axially extend from the hub 98. The arm may function to axially align the sheath 90 and the endoscope 60. The arm 108 may include a socket 102, fingers 109, an undercut 104, or a combination thereof as discussed herein. The arm 108 may function to contact the endoscope 60 so that the sheath 90 is positioned at a standard position, a predetermined position, or both relative to the endoscope 60. The arm 108 may function to align the distal end 92 of the sheath 90 with the distal end 62 of the endoscope 60. The arm 108 may function to extend the sheath 90 towards the proximal end 64 of the endoscope 60. The arm 108 may mirror the shape of the endoscope 60. The arm 108 may axially extend so that the arm 108 does not interfere with the visual port 74. The arm 108 may have an "L" shape. The arm 108 may extend down towards the endoscope 60 and then turn and extend axially along the endoscope 60. The arm 108 may be tapered. The arm 108 may be widest at its proximal end and thinnest at its distal end. The arm 108 may have a continuous width along its length. The arm 108 may include one or more hinges so that the angle of the arm 108 relative to the endoscope 60 may be varied. The arm 108 may include one or more flexible regions so that the angle of the arm 108 relative to the endoscope 60 may be varied. The arm 108 may be variable in length. The arm 108 may include a telescoping feature so that the endoscope 60 may be lengthened and shortened. The arm 108 may include one or more locking features that allow for the length of the arm 108 to be changed and then locked into position. The arm 108 may locate the sheath 90 relative to the endoscope 60 so that a flare 110, a facing surface 112, or both of the sheath 90 align with the endoscope 60.

The flare 110 may function to create a sealed connection with the endoscope 60. The flare 110 may create a fluid seal with the endoscope 60 so that irrigation fluid, suction, or both cannot escape between the endoscope 60 and the flare 110. The flare 110 may create a thrust seal. The thrust seal may be formed by the flare 110 compressing. The flare 110 may create a thrust seal, a circumferential seal, or both. The flare 110 may be axially compressed, radially compressed, radially expanded, or a combination thereof. The thrust seal may be formed between the shoulder 70 of the endoscope 60 and the flare 110 of the sheath 90. The flare 110 may substantially encircle a portion of the endoscope 60 so that when a thrust seal is created a fluid seal is created between the endoscope 60 and the sheath 90 and fluid is prevented from exiting the sheath 90 proximate to the endoscope 60. The flare 110 may be flexible so that the flare 110 forms a seal. The flare 110 may be elastically deformable so that the flare 110 forms a compression fitting with the endoscope 60. The flare 110 may be partially deformable, include a deformable region, include rubber, include an elastomer, include elastic, or a combination thereof. The flare 110 may be axially compressed when the endoscope 60 is inserted in the sheath 90. The flare 110 may form a circumferential seal about a shoulder 70 of the endoscope 60, an end of the proximal end region, around the tube 96, or a combination thereof. The flare 110 may axially extend from the hub 98 of sheath 90. The flare 110 may radially extend from the hub 98. The flare 110 may be located partially within the hub 98 and partially out of the hub 98. The flare 110 may have a facing surface 112 that contacts an endoscope 60.

The facing surface 112 may function to create a seal with an endoscope 60. The facing surface 112 may contact a shoulder 70 of the endoscope 60. The facing surface 112 may create a seal with the endoscope 60, the shoulder 70 of the endoscope 60, or both. The facing surface 112 may surround a portion of the endoscope 60. For example, the facing surface 112 may extend around the tube 96, the shoulder 70, or both to create a seal. The facing surface 112 may be made of a pliable material that forms a seal. The facing surface 112 may be made of an elastomer, may include an elastomer, or both. The facing surface 112 may elastically deform. The facing surface 112 may extend from the hub 98. The facing surface 112 may have a portion that extends radially outward. The hub 98 may include one or more spacers 128.

The one or more spacers 128 may function to axially align the endoscope 60 within the sheath 90. The one or more spacers 128 may contact a shoulder 70 of the endoscope 60 and align the endoscope 60 within the sheath 90. The spacer 128 may contact a tube so that the tube 96 is axially aligned within the tube. The one or more spacers 128 may be optional. The spacer 128 may be located proximate to one or more O-rings 130.

The one or more O-rings 130 may function to form a seal between the sheath 90 and a tube of the endoscope 60. The one or more O-rings 130 may function to prevent fluid from traveling towards the proximal end 64 of the endoscope 60. The one or more O-rings 130 may function to create a seal. The one or more O-rings 130 may be located within the hub 98, proximate to a collar 100 of the hub 98, or both. The one or more O-rings 130 may be made of any material that forms a seal. The one or more O-rings 130 may create a circumferential seal, a thrust seal, or both. The one or more O-rings 130 may be axially compressed, radially compressed, radially expanded, or a combination thereof. The one or more O-rings 130 may include one or more through holes 152. The one or more O-rings 130 may elastically deform. The one or more O-rings 130 may be made of an elastomer, include elastic, include rubber, include a deformable material, include a deformation region, or a combination thereof. The one or more O-rings 130 may be located proximate to a locking ring 132.

The one or more locking rings 132 may lock the O-ring 130 to the sheath 90, the endoscope 60, or both. The one or more locking rings 132 may function to lock two or more components together. The one or more locking rings 132 may include a through hole 152 so that the endoscope 60 extends through the tube 96 and the locking ring 132.

A through hole 152 may extend from a proximal end 94 to a distal end 92 of the sheath 90. A through hole 152 may be sufficiently large so that the endoscope 60 and fluid may pass from the distal end 92 to the proximal end 94 of the sheath. The tube 96 may include one or more through holes 152 in the sheath 90.

FIG. 1A illustrates a top view of sheath 90 for use with an endoscope cleaner system (not shown). The sheath 90 includes a distal end 92 and a proximal end 94. A tube 96 and hub 98 extend between the distal end 92 and the proximal end 94. The hub 98 includes a port 106 for receiving suction, an irrigation fluid, or both. The hub 98 also includes a collar 100 that includes a socket 102 for receiving a light post 72 (not shown) of a corresponding device (not shown).

Figure 1B:
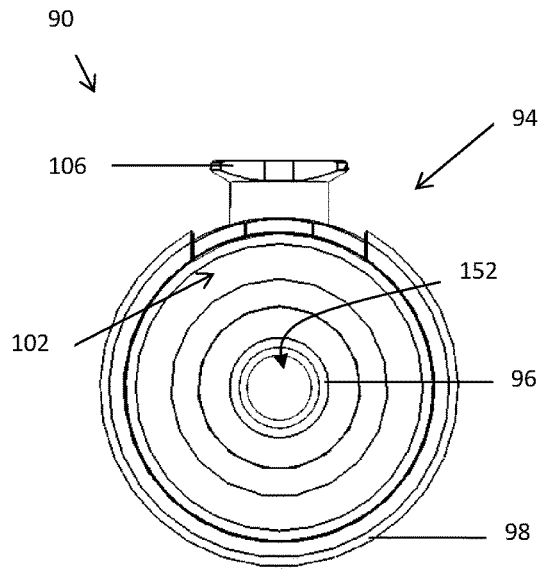
FIG. 1B illustrates a proximal end view of an endoscope sheath of FIG. 1A.

FIG. 1B illustrates an end view of the sheath 90 from the proximal end 94. The port 106 is shown extending from the hub 98 and a through hole 152 is shown extending through the tube 96 and hub 98. The socket 102 is illustrated extending through the hub 98 towards the port 106.

Figure 1C:
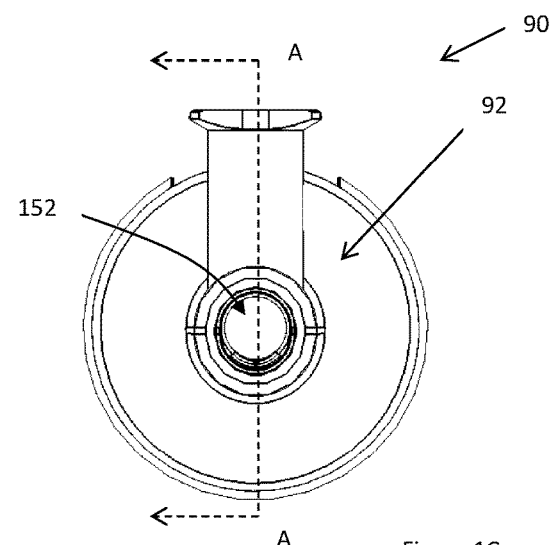
FIG. 1C illustrates a distal end view of an endoscope sheath of FIG. 1A.

FIG. 1C illustrates a view of the sheath 90 from the distal end 92. A through hole 152 is shown extending through the sheath 90.

Figure 2:
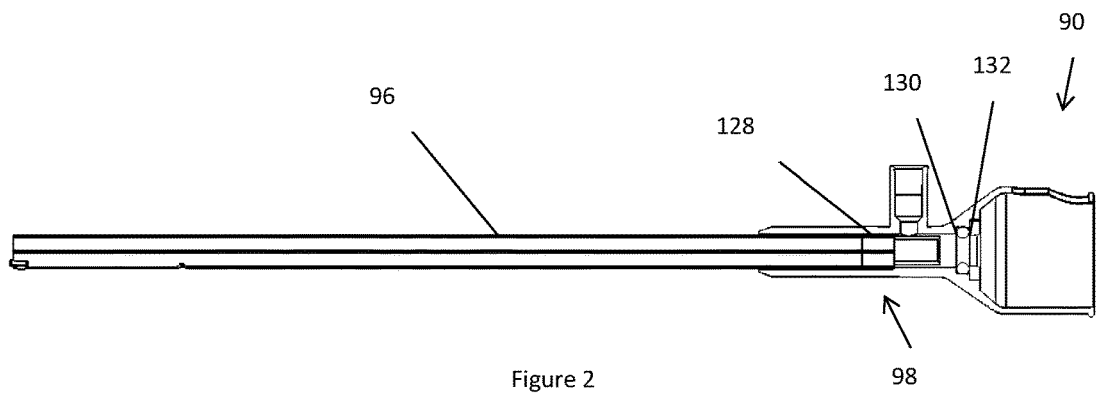
FIG. 2 illustrates a cross sectional view of FIG. 1C along lines A-A.

FIG. 2 illustrates a cross sectional view of the sheath 90 of FIG. 1C cut along lines A-A of FIG. 1C. The sheath 90 includes a tube 96 connected to a hub 98. The hub 98 includes a spacer 128 between an end of the tube 96 and a mating surface of the hub 98. An O-ring 130 is located in the hub proximate to a locking ring 132 for securing the O-ring to the hub 98

Figure 3A:
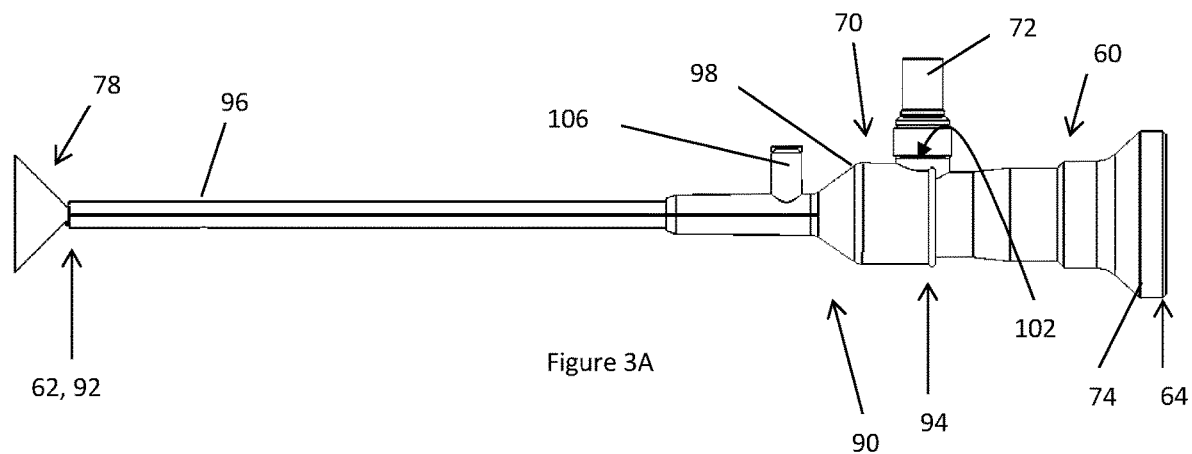
FIG. 3A illustrates a side view of an endoscope inserted in the endoscope sheath of FIG. 1A.

FIG. 3A illustrates an endoscope 60 extending into a sheath 90. The endoscope 60 includes a proximal end 64 including a visual port 74. The endoscope 60 includes a distal end 92 that extends to a distal end 62 of a sheath 90. The sheath 90 includes a tube 96 extending from a distal end 92 to a hub 98. A viewing cone 78 is shown extending at an angle (e.g., 0 degree angle) from the end of the endoscope 60 and sheath 90. The hub 98 includes a port 106 for receiving suction, an irrigation fluid, or both. The hub 98 terminates at a proximal end 94 by the hub 98 contacting a shoulder 70 of the endoscope 60 and the socket 102 of the sheath 90 receiving a light port 72 of the endoscope 60.

Figure 3B:
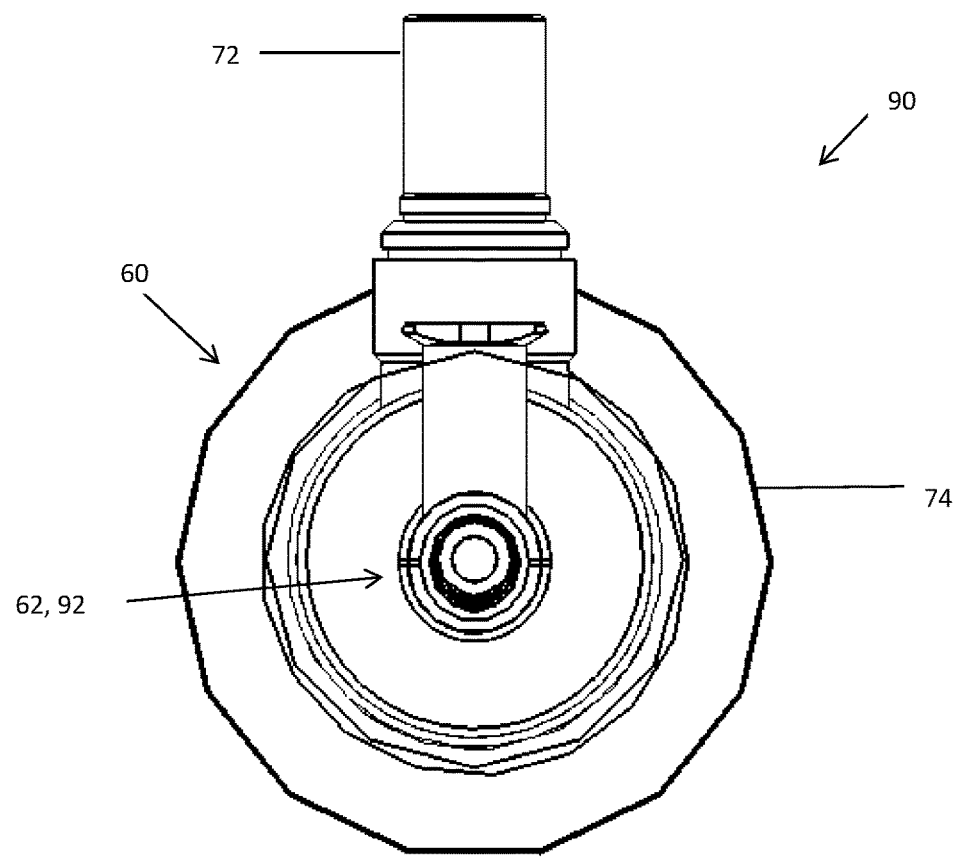
FIG. 3B illustrates a distal end view of FIG. 3A.

FIG. 3B illustrates an end view of the sheath 90 and endoscope 60 from a distal end view 62, 92. The visual port 74 and light post 72 of the endoscope 60 extend outward from the endoscope 60.

Figure 4A:
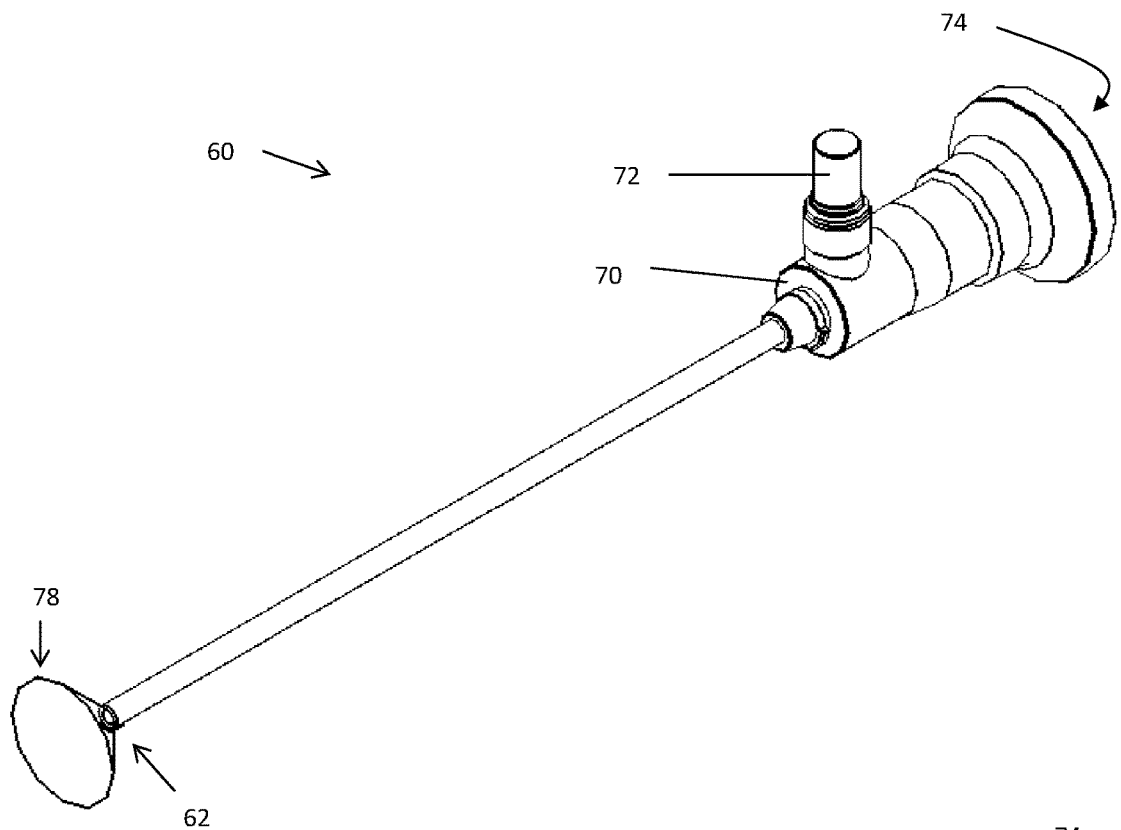
FIG. 4A illustrates an example of an endoscope with an imaging device at a 0 degree angle.

FIG. 4A illustrates an endoscope 60. The endoscope 60 includes a visual port 74 for providing an image. The visual port 74 provides an image that is located within the viewing cone 78 at the distal end 62 of the endoscope 60 which extends at a 0 degree angle. The endoscope 60 also includes a light port 72 for providing light to the distal end 62 of the endoscope. The endoscope 60 also includes a shoulder 70 to prevent the endoscope 60 from entering a patient.

Figure 4B:
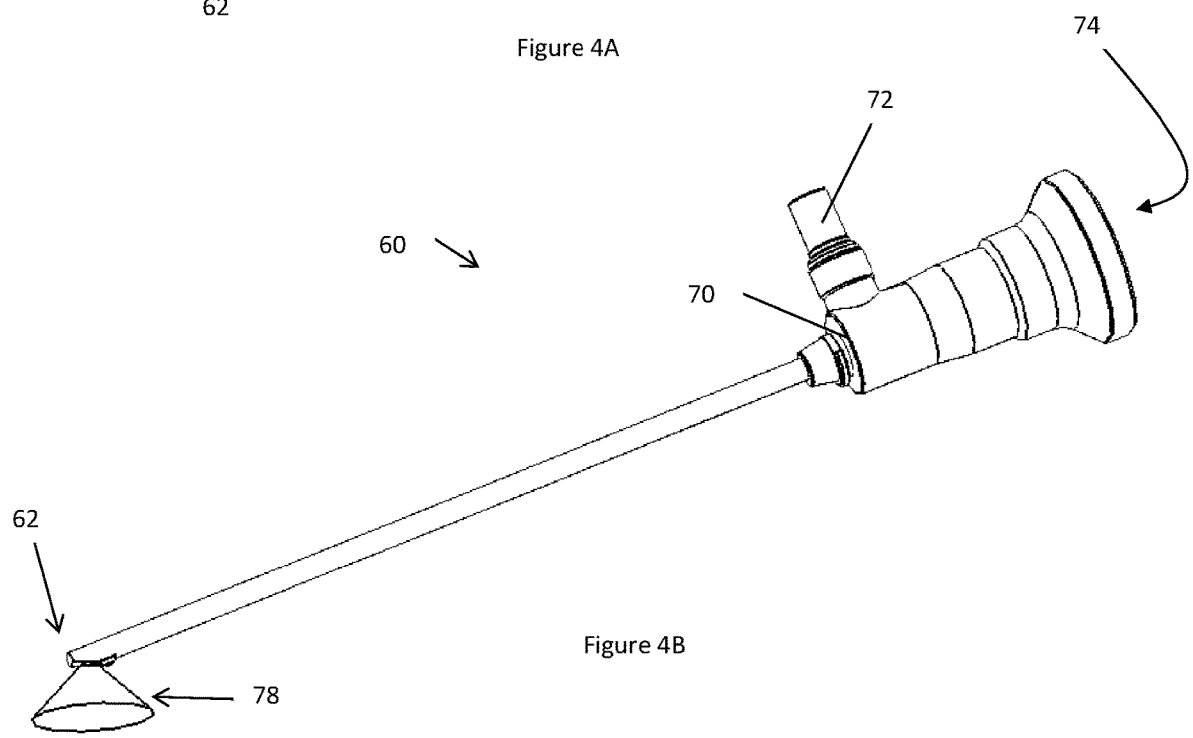
FIG. 4B illustrates an example of an endoscope with an imaging device at a 70 degree angle.

FIG. 4B illustrates an endoscope 60 having visual port 74 for viewing an image within the viewing cone 78 that is located at the distal end 62. The viewing cone 78 extends at a 70 degree angle from the distal end 62. A light post 72 and shoulder 70 are located proximate to the visual port 74.

FIG. 5 illustrates a perspective view of the sheath 90. The sheath 90 has a longitudinal axis 95 that extends through the hub 98 and tube 96 that are connected. The hub 98 is connected to an arm 108 that includes a socket 102, a pair of fingers 109, and an undercut 104 on each finger 109. The socket 102 has an opening for receiving a light post of an endoscope (not shown) for aligning the sheath 90 on the endoscope and the undercuts 104 retain the light post within the opening of the socket 102. A flare 110 and socket 102 are located on the proximal end 94 near the arm 108 and are configured to receive a portion of an endoscope. A port 106 extends from the tube 96 from a location adjacent to and on a distal side of the arm 108.

FIG. 6 illustrates a cross-sectional view of a sheath 90. The sheath 90 includes a hub 98 that is connected to a tube (not shown) with a longitudinal axis 95 extending through the tube and hub 98. A port 106 and an arm 108 extend from a same side of the hub 98 and the arm 108 is located proximal of the port 106. The tube 96 has a proximal end 94 with a flare 110 and facing surface 112 at the proximal end 94. The arm 108 includes a socket 102 for receiving a light post of an endoscope (not shown). The socket 102 includes fingers 109 that extend around an opening in the socket 102 and an undercut 104 at the end of the fingers 109. The opening of the socket 102 receives a light post (not shown) and the undercut 104 retains the light post within the opening.

Figure 7A:
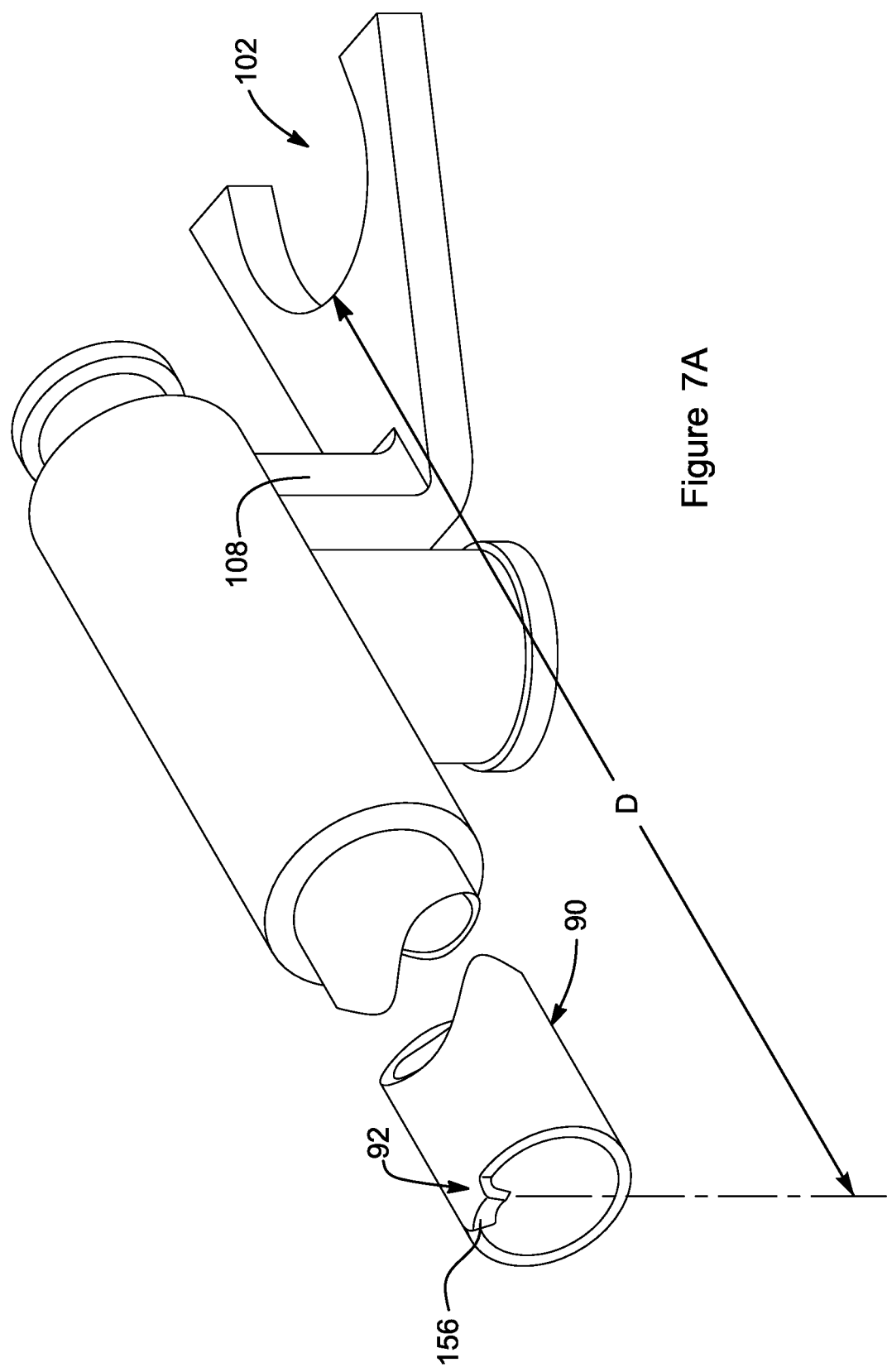
FIG. 7A illustrates a side view of an example of an endoscope sheath including an arm.

FIG. 7A illustrates a side view of another possible sheath 90. The sheath 90 includes a hooking portion 156 at a distal end 92 and an arm 108 extending from the sheath 90. The arm 108 is located so that the arm 108 aligns the hooking portion 156 on an endoscope (not shown) so that the hooking portion 156 directs a cleaning fluid across the endoscope and cleans the endoscope. The arm 108 includes a socket 102 that is configured to receive a portion of an endoscope such as a light post. The socket 102 includes a rear wall that is located a distance (D) from the hooking portion 156.

FIG. 7B illustrates a sheath 90 including a hooking portion 156 at the distal end 92. An arm 108 extends from the sheath 90 and aligns the hooking portion 156 with an end of an endoscope (not shown) so that a cleaning fluid is directed across a lens of the endoscope by the hooking portion 156. The hooking portion 156 extends further out than the hooking portion of FIG. 7A. The hooking portion 156 is located a distance (D2) from the rear wall of the socket 102.

Figure 8:
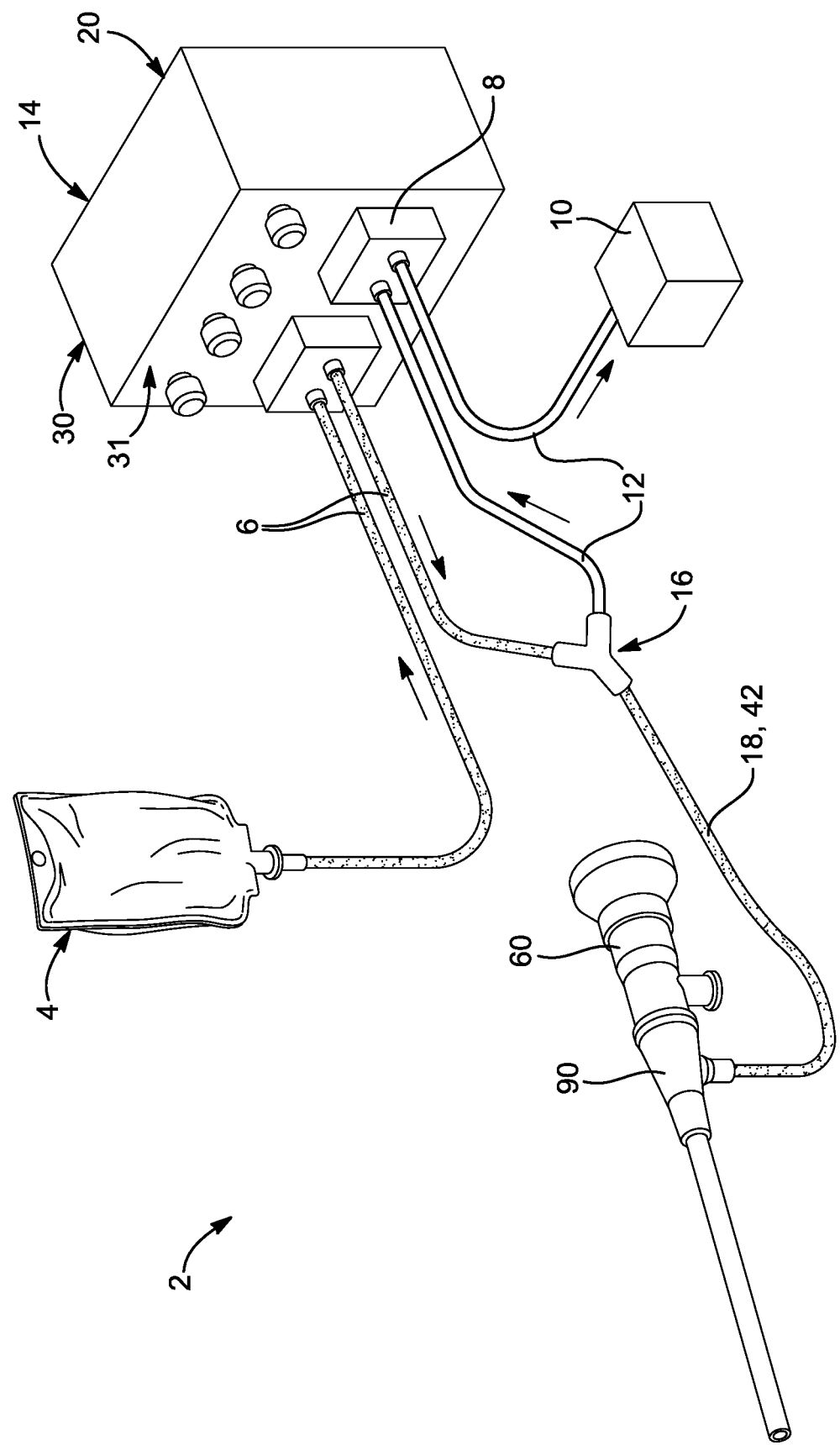
FIG. 8 illustrates an example of a system including the endoscope sheath of the teachings herein.

FIG. 8 illustrates an endoscope cleaning system 2. The endoscope cleaning system 2 includes an irrigation source 4 connected to an irrigation line 6 that is connected to a control module 30 that includes a pump 14 for controlling flow of irrigation fluid between the irrigation source 4 and a sheath 90. The control module 30 includes a power source 20 and a controller and/or microprocessor (not shown) that is in communication with a user interface 31 for controlling the control module 30. The system 2 includes a suction source 10 that is connected to the control module 30. The control module 30 includes a valve 8 in the suction line that is connected to a sheath 90, which receives a portion of an endoscope. The valve 8 for controls suction between the suction source 10 and the sheath 90 so that suction may be turned off during all or portion of the application cycle of the irrigation fluid. The irrigation line 6 and the suction line 12 are connected together at a common fitting 16 that connects the irrigation line 6 and the suction line 12 to a common line 18/delivery line 42 for supplying a fluid or suction to the sheath 90 for cleaning an endoscope (not shown).

Figure 9:
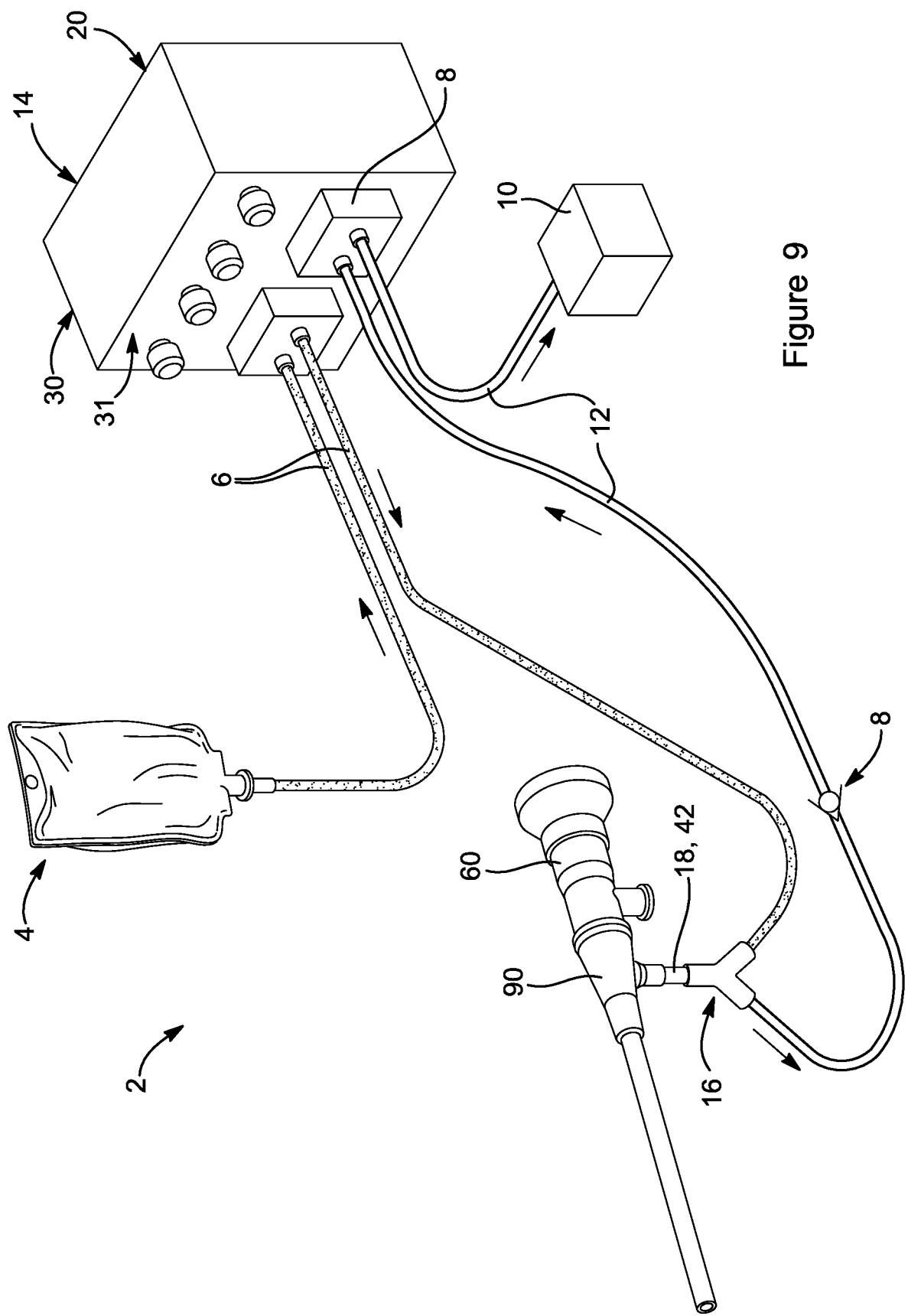
FIG. 9 illustrates another example of a system including the endoscope sheath of the teachings herein.

FIG. 9 illustrates a control module 30 that includes a pump 14, a power source 20, a user interface 31, and one or more valves 8. The irrigation source 4 is gravity fed into the pump 14 and then the pump 14 sends fluid through the irrigation line 6 to the sheath 90 so that the sheath 90 washes the endoscope 60. The suction source 10 is connected to a valve 8 of the control module 30 that controls suction being drawn through the suction lines 12. Both the irrigation lines 6 and the suction lines 12 are connected to a common fitting 16 and a single common line 18/delivery line 42 extend from the common fitting 16 to the sheath 90. The suction line 12 may include a valve 8 that is a passive check valve to prevent irrigation fluid from being forced into the suction line.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An endoscope sheath comprising:
   a. a tube extending along a longitudinal axis and configured to receive at least a portion of a shaft of an endoscope, the endoscope including a light post; and
   b. an arm attached to and extending from the endoscope sheath, the arm is configured to engage the light post;
   wherein a proximal end of the endoscope sheath includes a flare that is configured to form a fluid seal with a shoulder of the endoscope upon the arm engaging the light post, the fluid seal is configured to prevent one or more fluids from escaping between the flare and the shoulder; and wherein the shoulder of the endoscope is generally orthogonal to the longitudinal axis of the tube.

2. The endoscope sheath of claim 1, wherein at least a portion of the flare is elastically deformable, is circular, is configured to be axially compressed against the shoulder of the endoscope to form the fluid seal, and comprises a through hole that is configured for the portion of the shaft to extend through.

3. The endoscope sheath of claim 2, wherein the flare comprises a first portion having a first outer diameter and a second portion having a second outer diameter, the first outer diameter is larger than the second outer diameter.

4. The endoscope sheath of claim 3, wherein the first portion is located on a distal end of the endoscope sheath and the second portion is located proximal to the first portion.

5. The endoscope sheath of claim 1, wherein the endoscope sheath includes a port that is configured to provide the one or more fluids into the endoscope sheath, and
wherein the port is located distal of the flare.

6. An assembly comprising the endoscope sheath according to claim 1 and the endoscope.

7. The endoscope sheath of claim 1, wherein the arm comprises a proximal-most end that extends proximally beyond a proximal-most end of the flare.

8. The endoscope sheath of claim 7, wherein upon the arm engaging the light post, an outer circumferential surface of a proximal end region of the endoscope that is located immediately proximal to the shoulder of the endoscope is free from being entirely encircled within the endoscope sheath.

9. The endoscope sheath of claim 8, wherein the flare is configured to elastically deform when the arm engages the light post.

10. The endoscope sheath of claim 1, wherein upon the arm engaging the light post, an outer circumferential surface of a proximal end region of the endoscope that is located immediately proximal to the shoulder of the endoscope is free from being encircled within the endoscope sheath.

11. The endoscope sheath of claim 1, wherein the arm comprises a proximal-most end that extends proximally beyond a proximal-most end of the flare.

12. The endoscope sheath of claim 1, wherein the flare comprises a first portion having a first outer diameter and a second portion having a second outer diameter, the first outer diameter is larger than the second outer diameter, the second portion is located proximal to the first portion.

13. An endoscope sheath comprising:
a port for ingress of a fluid, suction, or both; and
a sealing feature that a portion of an endoscope is configured to extend through;
wherein the sealing feature is configured to deform to form a fluid seal with a shoulder of the endoscope.

14. The endoscope sheath according to claim 13, wherein the sealing feature is a flare, and the endoscope sheath comprises an arm that is configured to engage a light post of the endoscope,
wherein the flare is configured to be compressed against the shoulder to form the fluid seal with the shoulder of the endoscope upon the arm engaging the light post, and
wherein upon the arm engaging the light post, an outer circumferential surface of a proximal end region of the endoscope that is located immediately proximal to the shoulder of the endoscope is free from being encircled within the endoscope sheath.

15. The endoscope sheath of claim 14, wherein the sealing feature comprises an O-ring, the endoscope sheath comprises a locking ring that is configured to lock the O-ring to the endoscope sheath; and
wherein the locking ring comprises a through hole for a portion of the endoscope to extend through.

16. The endoscope sheath of claim 15, wherein the O-ring comprises a through hole and the endoscope sheath comprises a tube with a through hole, and
wherein the through hole of the O-ring, the through hole of the locking ring, and the through hole of the tube are all aligned along a common longitudinal axis.

17. The endoscope sheath of claim 13, wherein the endoscope sheath comprises a collar that is configured to engage a light post of the endoscope, the sealing feature is configured to elastically deform when the collar engages the light post.

18. An assembly comprising the endoscope sheath according to claim 13 and the endoscope.

19. The endoscope sheath of claim 13, wherein the endoscope sheath comprises an arm, and the endoscope comprises a light post,
wherein upon the arm engaging the light post, an outer circumferential surface of a proximal end region of the endoscope that is located immediately proximal to the shoulder of the endoscope is free from being entirely encircled within the endoscope sheath.

20. The endoscope sheath of claim 19, wherein the arm comprises a proximal-most end that extends proximally beyond a proximal-most end of the flare, and
wherein the flare is configured to elastically deform when the arm engages the light post.

* * * * *